United States Patent
Liu

(10) Patent No.: US 6,403,054 B1
(45) Date of Patent: *Jun. 11, 2002

(54) TERNARY LIGAND COMPLEXES USEFUL AS RADIOPHARMACEUTICALS

(75) Inventor: Shuang Liu, Chelmsford, MA (US) 01823

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/864,586

(22) Filed: May 28, 1997

(51) Int. Cl.$^7$ ............................. A61K 51/04; C07F 5/00
(52) U.S. Cl. ........................ 424/1.65; 424/1.77; 534/10; 534/14
(58) Field of Search ................................ 424/1.65, 1.77; 534/10, 11, 12, 13, 14, 15, 16

(56) References Cited

U.S. PATENT DOCUMENTS

| | | |
|---|---|---|
| 5,206,370 A | 4/1993 | Schwartz et al. ........... 546/281 |
| 5,350,837 A | 9/1994 | Bridger et al. ............... 534/14 |
| 5,589,576 A * | 12/1996 | Archer et al. ................ 534/14 |

FOREIGN PATENT DOCUMENTS

| | | |
|---|---|---|
| EP | 0441953 | 8/1991 |
| WO | 8908657 | 9/1989 |
| WO | 9410149 | 5/1994 |
| WO | 9614879 | 5/1996 |
| WO | 9631243 | 10/1996 |
| WO | 9640637 | 12/1996 |

OTHER PUBLICATIONS

Edwards et al., "New and Versatile Ternary Ligand System for Technetium Radiopharmacetics: Water Soluble Phosphines and Tricine as Coligands in Labeling a Hydrazinonicotinamide–Modified Cyclic Glycoprotein 11b/IIIa Receptor Antagonists with 99mTc", Bioconjugate Chem. 1977, 8, pp. 146–154.

Nicholson et al, Monomeric Five–Coordinate Rhenium Diazenido and Hydrazido Complexes with Aromatic Thiolate Ligands: X–Ray Structures of [Re(NNC$_6$H$_4$—4—Br)$_2$(SC$_6$H$_3$—2,5—Me$_2$)(PPh$_3$)$_2$], Polyhedron 1987,6, 1577–1585.

Dilworth et al, The Preparation and Substitution Chemistry of the Cationic Bis(Hydrazido(2–)) Rhenium (VII) Complex [ReCl$_2$(NNMePh)$_2$(PPh$_3$)][BPh$_4$], The Crystal and Molecular Structures of [Re(NNMePh)$_2$(S$_2$CNMe$_2$][BPh$_4$]and [ReOCl(NNMePh) (PPh$_3$)$_2$][PF$_6$]$_2$Month not available, Polyhedron 1992, 11, 147–155.

Dilworth et al, Crystal Structure of a Diazendido–Dithiocarbamate Complex of Technetium, [Tc(NNC$_6$H$_4$Cl) ((CH$_3$)$_2$NCS$_2$)$_2$(PPH$_3$)], Z. Naturforsch 1991, 46b, 449–452.

Archer et al, Development of New Technetium Cores Containing Technetium–Nitrogen Multiple Bonds, Synthesis and Characterization of some Diazenido–, Hydrazido–and Imido–Complexes of Technetium, Polyhedron 1990, 9, 1497–1502.

Archer et al, Technetium Diazenido Complexes. Part 1. Syntheses and Structures of [TcCl(NNC$_6$H$_4$Cl—4)$_3$(PPh$_3$)$_2$] and [TcCl (NNPh) (Ph$_2$PCH$_2$CH$_2$PPh$_2$)$_2$][PF$_6$].H$_2$O, J. Chem. Soc., Dalton Trans. 1993, 897–904.

Dilworth et al, Technetium Diazenido Complexes. Part 2. Substitution Chemistry of [TcCl(NNC$_6$H$_4$Cl—4)$_2$(PPh$_3$)$_2$] and the Synthesis of Technetium Diazenido–complexes Directly from [NH$_4$][TeO$_4$], J. Chem. Soc., Dalton Trans. 1994, 1251–1256.

Liu et al. "Labeling a Hydrazino Nicotinamide–Modified cyclic IIb/IIIc, Receptor Antagonist with 99mTc Using Aminocarboxylates as Coligands", Bioconugate Chem., pp. 63–71, vol. 7, No. 1 1996.*

* cited by examiner

Primary Examiner—Jose' G. Dees
Assistant Examiner—Michael G. Hartley
(74) Attorney, Agent, or Firm—David H. Vance; Peter L. Dolan

(57) ABSTRACT

The present invention provides novel radiopharmaceuticals useful for imaging the heart, brain, lungs, liver or kidneys, kits useful for preparing the radiopharmaceuticals, and methods of imaging the heart, brain, lungs, liver or kidneys in a patient in need of such imaging. The radiopharmaceuticals are comprised of technetium or rhenium radionuclide complexes of a ternary ligand system: one hydrazido or diazenido ligand, one aminoalcohol ligand, and one pi-acid ligand selected from phosphines, arsines, and imine nitrogen-containing heterocycles. The radiopharmaceuticals have the formula, $ML^1L^2L^3$, wherein the variables are as defined herein.

30 Claims, No Drawings

TERNARY LIGAND COMPLEXES USEFUL AS RADIOPHARMACEUTICALS

FIELD OF INVENTION

The present invention provides novel radiopharmaceuticals useful for imaging the heart, brain, lungs, liver or kidneys, kits useful for preparing the radiopharmaceuticals, and methods of imaging the heart, brain, lungs, liver or kidneys in a patient in need of such imaging.

BACKGROUND OF THE INVENTION

Radiopharmaceuticals form the chemical basis for the medical specialty of nuclear medicine, a group of techniques used for diagnosis and therapy of a variety of diseases. In vivo diagnostic information is obtained by intravenous injection of the radiopharmaceutical and determining its biological distribution using a gamma camera. The distribution usually takes a form that is organ or lesion specific. From the distribution of the radiopharmaceutical and its behavior over time, it is possible to obtain information about the presence, progression and state of a disease.

Radiopharmaceuticals useful for imaging the heart based on homoleptic Tc-99m-isonitrile complexes have been described by Jones et. al. in U.S. Pat. No. 4,452,774 and Bergstein et. al. in U.S. Pat. No. 4,988,827. Radiopharmaceuticals based on technetium-99m complexes of binary ligand systems have been described by Bergstein et. al. in U.S. Pat. No. 5,279,811 for imaging the brain, Kelly et. al. in U.S. Pat. No. 5,045,302 for imaging the heart, Nosco in U.S. Pat. No. 5,330,738 for imaging the kidneys, as well as others. A recent review of radiopharmaceuticals based on metal radionuclide complexes is provided by Jurisson et. al., Chem. Rev. 1993, 93, 1137.

The biological properties of metal radionuclide complexes are determined by their chemical and physical properties, such as lipophilicity and charge, as opposed to conjugates of a metal radionuclide complex and a biologically active molecule in which the biological properties of the conjugate are determined by the biologically active molecule. The chemical and physical properties of the complexes are determined by the ligand system used and the choice of the substituents on the ligand or ligands. Therefore, for any particular ligand system, the choice of substituents will control the biological properties of the complex and the ultimate utility as a radiopharmaceutical. An example of this effect is the fact that the Tc-99m complex of N,N'-1,2-ethylenediyl-bis-L-cysteine diethyl ester (ECD) is a brain imaging agent while the Tc-99m complex of N,N'-1,2-ethylenediyl-bis-L-cysteine (EC), in which the two ester groups are replaced by carboxylic acid groups, is a renal imaging agent.

For metal radionuclide complexes with a homoleptic ligand system, such as the Tc-99m-isonitriles, Tc(CNR)$_6^+$, a change in the substituent, R, is replicated six times, making it difficult to precisely control the chemical and physical properties of the complexes. For complexes comprised of a binary ligand system the substituents can be independently changed on the two types of ligands, giving somewhat better control. Superior control of the properties should be achievable for complexes comprised of a ternary ligand system in which the substituents on the three types of ligands can be independently varied. However, as the order of the ligand system increases the probability of forming complexes of one single stoichiometry is expected to decrease.

Archer et. al., European Patent Application 90914225.9 describes a series of technetium-99m complexes having a ternary ligand system comprised of a hydrazido or diazenido ligand, a phosphine ligand and a halide, in which the substituents on the hydrazido or diazenido ligand and those on the phosphine ligand can be independently varied; the halide ligand has no substituents. This disclosure does not teach or suggest how to achieve the superior control of biological properties that would result from a ternary ligand system in which the substituents on the three types of ligands can be independently varied.

Another important consideration for any radiopharmaceutical is specific activity, the amount of the radiopharmaceutical present in a dosage to the amount of unlabeled excess ligand or ligands used to synthesize the radiopharmaceutical. High specific activity is required when one or more of the ligands are either potentially toxic, very expensive to manufacture, or may compete with the radiopharmaceutical for a binding site in vivo, to minimize the amount of excess ligand in the dosage administered. The radiopharmaceuticals described by Archer et. al. are formed in low specific activity. Therefore, there remains a need for new radiopharmaceuticals comprised of a ternary ligand system for which the substituents on all three ligands can be independently varied and that can be formed in high specific activity.

SUMMARY OF THE INVENTION

The present invention provides novel radiopharmaceuticals useful for imaging the heart, brain, lungs, liver or kidneys, kits useful for preparing the radiopharmaceuticals, and methods of imaging the heart, brain, lungs, liver or kidneys in a patient in need of such imaging. The radiopharmaceuticals are comprised of technetium or rhenium radionuclide complexes of a ternary ligand system: one hydrazido or diazenido ligand, one aminoalcohol ligand, and one pi-acid ligand selected from phosphines, arsines, and imine nitrogen-containing heterocycles. The radiopharmaceuticals can be formed in high specific activity, are stable in vitro, and their biological properties can be tailored by the selection of substituents on the three ligands.

DETAILED DESCRIPTION OF THE INVENTION

[1] In a first embodiment, the present invention provides a novel radiopharmaceutical of the formula:

or a pharmaceutically acceptable salt thereof, wherein,

M is $^{99m}$Tc, $^{186}$Re or $^{188}$Re;

$L^1$ is a ligand having the formula =N—NR$^1$R$^2$ or =N$^+$=NR$^1$;

$R^1$ is selected from the group: aryl substituted with 0–3 R$^3$, 5–10 membered heterocycle containing from 1–4 heteroatoms selected from N, O, and S and substituted with 0–3 R$^3$, C$_1$–C$_{10}$ alkyl substituted with 0–3 R$^3$, and C$_{3-13}$ cycloalkyl substituted with 0–3 R$^3$;

$R^2$ is selected from the group: hydrogen, aryl substituted with 0–3 R$^3$, 5–10 membered heterocycle containing from 1–4 heteroatoms selected from N, O, and S and substituted with 0–3 R$^3$, C$_1$–C$_{10}$ alkyl substituted with 0–3 R$^3$, and C$_{3-13}$ cycloalkyl substituted with 0–3 R$^3$;

$R^3$ is independently selected at each occurrence from the group: =O, F, Cl, Br, I, —CF$_3$, —CN, —CO$_2$R$^4$, —C(=O)R$^4$, —C(=O)N(R$^4$)$_2$, —CH$_2$OR$^4$, —OC(=O)R$^4$, —OC(=O)OR$^4$, —OR$^4$, —OC(=O)N(R$^4$)$_2$, —NR$^4$C(=O)R$^4$, —NR$^4$C(=O)OR$^4$, —NR$^4$C(=O)N (R⁴)₂, —NR⁴SO₂N(R⁴)₂, —NR⁴SO₂R⁴, —SO₃H, —SO₂R⁴, —S(=O)R⁴, —SO₂N(R⁴)₂, —N(R⁴)₂, —N(R⁴)₃⁺, —NHC(=NH)NHR⁴, —C(=NH)NHR⁴, =NOR⁴, —NO₂, —C(=O)NHOR⁴, —C(=O)NH(R⁴)₂, —OCH₂CO₂H, 2-(1-morpholino)ethoxy, $C_1$–$C_{10}$ alkyl substituted with 0–3 R⁵, $C_2$–$C_{10}$ alkenyl substituted with 0–3 R⁵, $C_3$–$C_6$ cycloalkyl substituted with 0–3 R⁵, aryl substituted with 0–3 R⁵, and 5–10 membered heterocycle containing from 1–4 heteroatoms selected from N, O, and S and substituted with 0–3 R⁵;

R⁴ is independently selected at each occurrence from the group: H, $C_1$–$C_{10}$ alkyl substituted with 0–3 R⁵, $C_2$–$C_{10}$ alkenyl substituted with 0–3 R⁵, $C_3$–$C_6$ cycloalkyl substituted with 0–3 R⁵, aryl substituted with 0–3 R⁵, and 5–10 membered heterocycle containing from 1–4 heteroatoms selected from N, O, and S and substituted with 0–3 R⁵;

R⁵ is independently selected at each occurrence from the group: =O, F, Cl, Br, I, —CF₃, —CN, —CO₂R⁶, —C(=O)R⁶, —C(=O)N(R⁶)₂, —CH₂OR⁶, —OC(=O)R⁶, —OC(=O)OR⁶, —OR⁶, —OC(=O)N(R⁶)₂, —NR⁶C(=O)R⁶, —NR⁶C(=O)OR⁶, —NR⁶C(=O)N(R⁶)₂, —NR⁶SO₂N(R⁶)₂, —NR⁶SO₂R⁶, —SO₃H, —SO₂R⁶, —S(=O)R⁶, —SO₂N(R⁶)₂, —N(R⁶)₂, —N(R⁶)₃⁺, —NHC(=NH)NHR⁶, —C(=NH)NHR⁶, =NOR⁶, —NO₂, —C(=O)NHOR⁶, —C(=O)NHNR⁶R⁶, —OCH₂CO₂H, and phenyl;

provided that when R¹ is pyridyl-R³, R³ is C(O)N(R⁴)₂, and one R₄ is alkyl-(R⁵)₂, then R⁵ at each occurrence is other than phenyl;

R⁶ is independently selected at each occurrence from the group: H, and $C_1$–$C_6$ alkyl;

L² is a ligand having the formula (R¹¹)(R¹²)(R¹³)C—N(R⁷)—(C(R⁸)(R⁹))ₘ—R¹⁰

R⁷ is selected from the group: hydrogen, hydroxy, aryl substituted with 0–3 R¹⁴, and $C_1$–$C_{10}$ alkyl substituted with 0–3 R¹⁵;

alternatively, R⁷ and R⁸ together form a 3–6 membered heterocycle containing from 1–4 heteroatoms selected from N, O, and S and substituted with 0–3 R¹⁴;

R⁸ and R⁹ are independently selected from the group: hydrogen, hydroxyl, 5–10 membered heterocycle containing from 1–4 heteroatoms selected from N, O, and S and substituted with 0–3 R¹⁴, $C_1$–$C_{10}$ alkyl substituted with 0–3 R¹⁵, and $C_{3-13}$ cycloalkyl substituted with 0–3 R¹⁵;

alternatively, R⁸ and R⁹ can be taken together to form a $C_3$–$C_6$ cycloalkyl substituted with 0–3 R¹⁵;

R¹⁰ is selected from the group: —COOH, phenyl substituted with 0–3 R¹⁴, and 5–10 membered heterocycle containing from 1–4 heteroatoms selected from N, O, and S and substituted with 0–3 R¹⁴;

R¹¹ and R¹² are independently selected at each occurrence from the group: H, —OH, —COOH, 5–10 membered heterocycle containing from 1–4 heteroatoms selected from N, O, and S and substituted with 0–3 R¹⁴, $C_1$–$C_{10}$ alkyl substituted with 0–3 R¹⁵, and $C_{3-13}$ cycloalkyl substituted with 0–3 R¹⁵;

alternatively, R⁷ and R¹¹ together form a 3–6 membered heterocycle containing from 1–4 heteroatoms selected from N, O, and S and substituted with 0–3 R¹⁴;

R¹³ is —CH₂OH, or —CH₂CH₂OH;

m is 0–2;

R¹⁴ is independently selected at each occurrence from the group: $C_1$–$C_5$ alkyl substituted with 0–3 R¹⁵, $C_2$–$C_5$ alkenyl substituted with 0–3 R¹⁵, $C_3$–$C_6$ cycloalkyl substituted with 0–3 R¹⁵, aryl substituted with 0–3 R¹⁵, and 5–10 membered heterocycle containing from 1–4 heteroatoms selected from N, O, and S and substituted with 0–3 R¹⁵, F, Cl, Br, I, —CF₃, —CN, —CO₂R¹⁶, —C(=O)R¹⁶, —C(=O)N(R¹⁶)₂, —CH₂OR¹⁶, —OC(=O)R¹⁶, —OC(=O)OR¹⁶, —OR¹⁶, —OC(=O)N(R¹⁶)₂, —NR¹⁶C(=O)R¹⁶, —NR¹⁶C(=O)OR¹⁶, —NR¹⁶C(=O)N(R¹⁶)₂, —NR¹⁶SO₂N(R¹⁶)₂, —NR¹⁶SO₂R¹⁶, —SO₃H, —SO₂R¹⁶, —SO₂N(R¹⁶)₂, —PO₃H₂, —NHC(=NH)NHR¹⁶, —C(=NH)NHR¹⁶, NO₂, —OCH₂CO₂H;

R¹⁵ is independently selected at each occurrence from the group: =O, F, Cl, Br, I, —CF₃, —CN, —CO₂R¹⁶, —C(=O)R¹⁶, —C(=O)N(R¹⁶)₂, —CH₂OR¹⁶, —OC(=O)R¹⁶, —OC(=O)OR¹⁶, —OR¹⁶, —OC(=O)N(R¹⁶)₂, —NR¹⁶C(=O)R¹⁶, —NR¹⁶C(=O)OR¹⁶, —NR¹⁶C(=O)N(R¹⁶)₂, —NR¹⁶SO₂N(R¹⁶)₂, —NR¹⁶SO₂R¹⁶, —SO₃H, —SO₂R¹⁶, —SO₂N(R¹⁶)₂, —PO₃H₂, —NHC(=NH)NHR¹⁶, —C(=NH)NHR¹⁶, NO₂, and —OCH₂CO₂H;

R¹⁶ is independently selected at each occurrence from the group: hydrogen, and $C_1$–$C_6$ alkyl;

L³ is a ligand having a formula selected from the group:

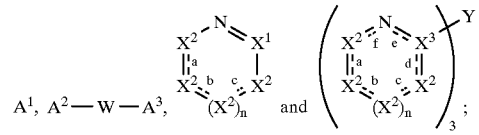

A¹ is selected from the group: PR¹⁷R¹⁸R¹⁹ and AsR¹⁷R¹⁸R¹⁹;

A² and A³ are independently selected at each occurrence from the group: PR¹⁷R¹⁸ and AsR¹⁷R¹⁸;

R¹⁷, R¹⁸, and R¹⁹ are independently selected at each occurrence from the group: aryl substituted with 0–3 R²⁰, 5–10 membered heterocycle containing from 1–4 heteroatoms selected from N, O, and S and substituted with 0–3 R²⁰, aralkyl substituted with 0–3 R²⁰, arylalkaryl substituted with 0–3 R²⁰, $C_1$–$C_{10}$ alkyl substituted with 0–3 R²¹, and $C_{3-13}$ cycloalkyl substituted with 0–3 R²¹;

W is a spacer group selected from the group: aryl substituted with 0–3 R²⁰, 5–10 membered heterocycle containing from 1–4 heteroatoms selected from N, O, and S and substituted with 0–3 R²⁰, aralkyl substituted with 0–3 R²⁰, $C_1$–$C_{10}$ alkyl substituted with 0–3 R²¹, and $C_{3-13}$ cycloalkyl substituted with 0–3 R²¹;

R²⁰ is independently selected at each occurrence from the group: $C_1$–$C_5$ alkyl substituted with 0–3 R²¹, $C_2$–$C_5$ alkenyl substituted with 0–3 R²¹, $C_3$–$C_6$ cycloalkyl substituted with 0–3 R²¹, aryl substituted with 0–3 R²¹, and 5–10 membered heterocycle containing from 1–4 heteroatoms selected from N, O, and S and substituted with 0–3 R²¹, F, Cl, Br, I, —CF₃, —CN, —CO₂R²², —C(=O)R²², —C(=O)N(R²²)₂, —CH₂OR²², —OC(=O)R²², —OC(=O)OR²², —OR²², —OC(=O)N(R²²)₂, —NR²²C(=O)R²², —NR²²C(=O)OR²², —N(R²²)₂, —N(R²²)₃⁺, —NR²²C(=O)N(R²²)₂, —NR²²SO₂N(R²²)₂, —NR²²SO₂R²², —SO₃H, —SO₂R²², —SO$_2$N(R$^{22}$)$_2$, —PO$_3$H$_2$, —NHC(=NH)NHR$^{22}$, —C(=NH)NHR$^{22}$, NO$_2$, and —OCH$_2$CO$_2$H;

R$^{21}$ is independently selected at each occurrence from the group: =O, F, Cl, Br, I, —CF$_3$, —CN, —CO$_2$R$^{22}$, —C(=O)R$^{22}$, —C(=O)N(R$^{22}$)$_2$, —CH$_2$OR$^{22}$, —OC(=O)R$^{22}$, —OC(=O)OR$^{22}$, —OR$^{22}$, —OC(=O)N(R$^{22}$)$_2$, —NR$^{22}$C(=O)R$^{22}$, —NR$^{22}$C(=O)OR$^{22}$, —NR$^{22}$C(=O)N(R$^{22}$)$_2$, —NR$^{22}$SO$_2$N(R$^{22}$)$_2$, —NR$^{22}$SO$_2$R$^{22}$, —SO$_3$H, —SO$_2$R$^{22}$, —S(=O)R$^{22}$, —SO$_2$N(R$^{22}$)$_2$, —N(R$^{22}$)$_2$, —N(R$^{22}$)$_3^+$, —PO$_3$H$_2$, —NHC(=NH)NHR$^{22}$, —C(=NH)NHR$^{22}$, =NOR$^{22}$, NO$_2$, —C(=O)NHOR$^{22}$, —C(=O)NHN(R$^{22}$)$_2$, —OCH$_2$CO$_2$H;

R$^{22}$ is independently selected at each occurrence from the group: hydrogen and C$_1$–C$_6$ alkyl;

X$^1$ is independently selected at each occurrence from the group: CR$^{23}$ and N;

X$^2$ is independently selected at each occurrence from the group: CR$^{23}$, CR$^{23}$R$^{23}$, N, NR$^{23}$, O and S;

X$^3$ is independently selected at each occurrence from the group: C, CR$^{23}$, and N;

provided the total number of heteroatoms, X$^1$, X$^2$, and X$^3$ in each ring of the ligand, L$^3$, is 1, 2, 3, or 4;

Y is selected from the group: BR$^{23-}$, CR$^{23}$, (P=O), (P=S);

n is 0 or 1;

a, b, c, d, e and f indicate the positions of optional double bonds, provided that one of e and f is a double bond;

R$^{23}$ is independently selected at each occurrence from the group: H, C$_1$–C$_{10}$ alkyl substituted with 0–3 R$^{24}$, C$_2$–C$_{10}$ alkenyl substituted with 0–3 R$^{24}$, C$_2$–C$_{10}$ alkynyl substituted with 0–3 R$^{24}$, aryl substituted with 0–3 R$^{24}$, C$_1$–C$_{10}$ alkoxy substituted with 0–3 R$^{24}$, C$_{3-13}$ carbocycle substituted with 0–3 R$^{24}$, and R$^{24}$;

or, alternatively, two R$^{23}$ may be taken together with the atom or atoms to which they are attached to form a fused aromatic substituted with 0–3 R$^{24}$, C$_{5-7}$ carbocyclic ring substituted with 0–3 R$^{24}$ or 5–7 membered heterocycle containing from 1–4 heteroatoms selected from N, O, and S, and substituted with 0–3 R$^{24}$;

R$^{24}$ is independently selected at each occurrence from the group: =O, F, Cl, Br, I, —CF$_3$, —CN, —NO$_2$, —CO$_2$R$^{25}$, —C(=O)R$^{25}$, —C(=O)N(R$^{25}$)$_2$, —N(R$^{25}$)$_3^+$, —CH$_2$OR$^{25}$, —OC(=O)R$^{25}$, —OC(=O)OR$^{25}$, —OR$^{25}$, —OC(=O)N(R$^{25}$)$_2$, —NR$^{25}$C(=O)R$^{25}$, —NR$^{25}$C(=O)OR$^{25}$, —NR$^{25}$C(=O)N(R$^{25}$)$_2$, —NR$^{25}$SO$_2$N(R$^{25}$)$_2$, —NR$^{25}$SO$_2$R$^{25}$, —SO$_3$H, —SO$_2$R$^{25}$, —SO$_2$N(R$^{25}$)$_2$, —N(R$^{25}$)$_2$, —OCH$_2$CO$_2$H; and R$^{25}$ is independently selected at each occurrence from the group: hydrogen and C$_1$–C$_6$ alkyl.

[2] In a preferred embodiment, the present invention provides novel radiopharmaceuticals, wherein:

M is $^{99m}$Tc;

R$^1$ is selected from the group: aryl substituted with 0–3 R$^3$, and 5–10 membered heterocycle containing from 1–4 heteroatoms selected from N, O, and S and substituted with 0–3 R$^3$;

R$^2$ is selected from the group: hydrogen, aryl substituted with 0–3 R$^3$, and 5–10 membered heterocycle containing from 1–4 heteroatoms selected from N, O, and S and substituted with 0–3 R$^3$;

R$^3$ is independently selected at each occurrence from the group: F, Cl, Br, I, —CO$_2$R$^4$, —C(=O)N(R$^4$)$_2$, —CH$_2$OR$^4$, —OC(=O)R$^4$, —OR$^4$, —NR$^4$C(=O)R$^4$, —NR$^4$SO$_2$R$^4$, —SO$_3$H, —SO$_2$N(R$^4$)$_2$, —N(R$^4$)$_2$, —N(R$^4$)$_3^+$, —NO$_2$, —OCH$_2$CO$_2$H, and C$_1$–C$_{10}$ alkyl substituted with 0–3 R$^5$;

R$^4$ is independently selected at each occurrence from the group: H, and C$_1$–C$_{10}$ alkyl substituted with 0–3 R$^5$;

R$^5$ is independently selected at each occurrence from the group: =O, F, Cl, Br, I, —CO$_2$R$^6$, —C(=O)N(R$^6$)$_2$, —CH$_2$OR$^6$, —OC(=O)R$^6$, —OR$^6$, —NR$^6$C(=O)R$^6$, —NR$^6$SO$_2$R$^6$, —SO$_3$H, —SO$_2$N(R$^6$)$_2$, —N(R$^6$)$_2$, —N(R$^6$)$_3^+$, —NO$_2$, —OCH$_2$CO$_2$H, and phenyl;

R$^7$ is selected from the group: hydrogen, and C$_1$–C$_{10}$ alkyl substituted with 0–3 R$^{15}$;

R$^8$ and R$^9$ are independently selected from the group: hydrogen, hydroxyl, and C$_1$–C$_{10}$ alkyl substituted with 0–3 R$^{15}$;

R$^{11}$ and R$^{12}$ are independently selected at each occurrence from the group: H, —OH, and C$_1$–C$_{10}$ alkyl substituted with 0–3 R$^{15}$;

m is 0–1;

R$^{14}$ is independently selected at each occurrence from the group: C$_1$–C$_5$ alkyl substituted with 0–3 R$^{15}$, F, Cl, Br, I, —CO$_2$R$^{16}$, —C(=O)N(R$^{16}$)$_2$, —CH$_2$OR$^{16}$, —OC(=O)R$^{16}$, —OR$^{16}$, —NR$^{16}$C(=O)R$^{16}$, —NR$^{16}$SO$_2$R$^{16}$, —SO$_3$H, —SO$_2$N(R$^{16}$)$_2$, —PO$_3$H$_2$, —NO$_2$, and —OCH$_2$CO$_2$H;

R$^{15}$ is independently selected at each occurrence from the group: =O, F, Cl, Br, I, —CO$_2$R$^{16}$, —C(=O)N(R$^{16}$)$_2$, —CH$_2$OR$^{16}$, —OC(=O)R$^{16}$, —OR$^{16}$, —NR$^{16}$C(=O)R$^{16}$, —NR$^{16}$SO$_2$R$^{16}$, —SO$_3$H, —SO$_2$N(R$^{16}$)$_2$, —PO$_3$H$_2$, and —OCH$_2$CO$_2$H;

L$^3$ is a ligand having a formula selected from the group:

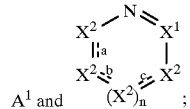

A$^1$ is PR$^{17}$R$^{18}$R$^{19}$;

R$^{17}$, R$^{18}$, and R$^{19}$ are independently selected from the group: aryl substituted with 0–3 R$^{20}$, 5–10 membered heterocycle containing from 1–4 heteroatoms selected from N, O, and S and substituted with 0–3 R$^{20}$, and C$_1$–C$_{10}$ alkyl substituted with 0–3 R$^{21}$;

R$^{20}$ is independently selected at each occurrence from the group: C$_1$–C$_5$ alkyl substituted with 0–3 R$^{21}$, F, Cl, Br, I, —CO$_2$R$^{22}$, —C(=O)N(R$^{22}$)$_2$, —CH$_2$OR$^{22}$, —OC(=O)R$^{22}$, —OR$^{22}$, —NR$^{22}$C(=O)R$^{22}$, —NR$^{22}$SO$_2$R$^{22}$, —SO$_3$H, —SO$_2$N(R$^{22}$)$_2$, —N(R$^{22}$)$_2$, —N(R$^{22}$)$_3^+$, —PO$_3$H$_2$, and —OCH$_2$CO$_2$H;

R$^{21}$ is independently selected at each occurrence from the group: =O, F, Cl, Br, I, —CO$_2$R$^{22}$, —C(=O)N(R$^{22}$)$_2$, —CH$_2$OR$^{22}$, —OC(=O)R$^{22}$, —PO$_3$H$_2$, —OR$^{22}$, —NR$^{22}$C(=O)R$^{22}$, —NR$^{22}$SO$_2$R$^{22}$, —SO$_3$H, —SO$_2$N(R$^{22}$)$_2$, —N(R$^{22}$)$_2$, —N(R$^{22}$)$_3^+$, and —OCH$_2$CO$_2$H;

x$^2$ is independently selected at each occurrence from the group: CR$^{23}$, CR$^{23}$R$^{23}$, N, NR$^{23}$, and O;

provided the total number of heteroatoms, X$^1$ and X$^2$, is 1, 2, 3, or 4;

R$^{23}$ is independently selected at each occurrence from the group: H, C$_1$–C$_3$ alkyl substituted with 0–3 R$^{24}$, aryl substituted with 0–3 R$^{24}$, and R$^{24}$;

alternatively, two R$^{23}$'s may be taken together with the atom or atoms to which they are attached to form a fused aromatic substituted with 0–3 $R^{24}$ or a 5–7 membered heterocyclic ring containing from 1–4 heteroatoms selected from N, O, and S and substituted with 0–3 $R^{24}$; and, $R^{24}$ is independently selected at each occurrence from the group: —$NO_2$, —$CO_2R^{25}$, —$OR^{25}$, —$SO_3H$, and —$OCH_2CO_2H$.

[3] In a further preferred embodiment, the present invention provides novel radiopharmaceuticals, wherein:

$R^1$ is selected from the group: aryl substituted with 0–1 $R^3$, and heterocycle substituted with 0–1 $R^3$, wherein said heterocycle is pyridine or phthalazine;

$R^2$ is selected from the group: hydrogen, and aryl substituted with 0–1 $R^3$;

$R^3$ is independently selected at each occurrence from the group: Cl, —$CO_2R^4$, —C(=O)N($R^4$)$_2$, —$OR^4$, —$SO_3H$, and —$NO_2$;

$R^4$ is independently selected at each occurrence from the group: H, and $C_1$–$C_{10}$ alkyl substituted with 0–2 $R^5$;

$R^5$ is selected from the group: —$CO_2R^6$, —$OR^6$, and phenyl;

$R^6$ is independently selected from the group: H and methyl;

$R^7$, $R^8$, and $R^9$ are each hydrogen;

$R^{10}$ is selected from the group: —COOH, and 2-hydroxyphenyl;

m is 0–1, provided that when $R^{10}$ is —COOH, m is 1;

$R^{11}$, $R^{12}$, and $R^{13}$ are each —$CH_2OH$;

$A^1$ is $PR^{17}R^{18}R^{19}$;

$R^{17}$, $R^{18}$ and $R^{19}$ are independently selected from the group: aryl substituted with 0–1 $R^{20}$, 5–10 membered heterocycle containing from 1–4 heteroatoms selected from N, O, and S and substituted with 0–1 $R^{20}$, and $C_1$–$C_3$ alkyl substituted with 0–1 $R^{21}$;

$R^{20}$ is independently selected at each occurrence from the group: —$CO_2R^{22}$, —$OR^{22}$, and —$SO_3H$;

$R^{21}$ is selected from the group: —$CO_2R^{22}$, and —$OR^{22}$;

$R^{22}$ is independently selected from the group: H, and methyl;

$X^1$ is CH; and, $X^2$ is independently selected at each occurrence from the group: CH, and NH, provided only one $X^2$ is NH.

[4] In an even further preferred embodiment, the radiopharmaceutical is selected from the group:

[$^{99m}$Tc(HYPY) (tricine) (TPPTS)];
[$^{99m}$Tc(HYPY) (tricine) (TPPMS)];
[$^{99m}$Tc(HYPY) (tricine) (imidazole)];
[$^{99m}$Tc(HYPY) (tricine) (pyridine)];
[$^{99m}$Tc(HYPY) (tricine) (TFP)];
[$^{99m}$Tc(HYPY) (tricine) (PPh$_3$)];
[$^{99m}$Tc(HYNICamide) (tricine) (TPPTS)];
[$^{99m}$Tc(HYNIC-DMA) (tricine) (TPPTS)];
[$^{99m}$Tc(HYNIC-Gly-OMe) (tricine) (TPPTS)];
[$^{99m}$Tc(HYNIC-D-Phe-OMe)(tricine)(TPPTS)];
[$^{99m}$Tc(DPH) (tricine) (TPPTS)];
[$^{99m}$Tc(DPH) (tricine) (TFP)];
[$^{99m}$Tc(DPH) (tricine) (TPPMS)];
[$^{99m}$Tc(DPH) (tricine) (PPh$_3$)];
[$^{99m}$Tc(11-(6-hydrazinonicotinamido)undecanoic acid) (tricine)(TPPTS)];
[$^{99m}$Tc(11-(6-hydrazinonicotinamido)undecanoic acid) (tricine)(imidazole)];
[$^{99m}$Tc(11-(6-hydrazinonicotinamido)undecanoic acid) (tricine)(pyridine)];
[$^{99m}$Tc(11-(6-hydrazinonicotinamido)undecanoic acid) (tricine)(TFP)];
[$^{99m}$Tc(PHY) (tricine) (TPPTS)];
[$^{99m}$Tc(HYLA) (tricine) (TPPTS)];
[$^{99m}$Tc(4-Cl-PHY) (tricine) (TPPTS)];
[$^{99m}$Tc(HYPY) (hbtris) (TPPTS)];
[$^{99m}$Tc(HYLA) (hbtris) (TPPTS)];
[$^{99m}$Tc(4-Cl-PHY) (hbtris) (TPPTS)]; and,
[$^{99m}$Tc(4-$NO_2$-PHY) (hbtris) (TPPTS)].

[5] In a second embodiment, the present invention provides a novel kit for preparing a radiopharmaceutical, comprising:

(a) a pharmaceutically acceptable first ligand having the formula $R^1R^2N$—$NH_2$ or a ligand precursor having the formula $R^1R^2N$—N=$CR^{26}R^{27}$;

(b) a pharmaceutically acceptable second ligand having the formula:

$$(R^{11})(R^{12})(R^{13})C-N(R^7)-(C(R^8)(R^9))_m-R^{10};$$

and, (c) a pharmaceutically acceptable third ligand having a formula selected from the group:

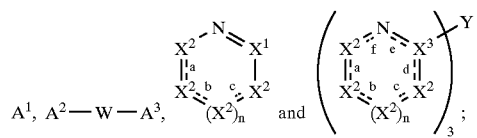

$R^1$ is selected from the group: aryl substituted with 0–3 $R^3$, 5–10 membered heterocycle containing from 1–4 heteroatoms selected from N, O, and S and substituted with 0–3 $R^3$, $C_1$–$C_{10}$ alkyl substituted with 0–3 $R^3$, and cycloalkyl substituted with 0–3 $R^3$;

$R^2$ is selected from the group: hydrogen, aryl substituted with 0–3 $R^3$, 5–10 membered heterocycle containing from 1–4 heteroatoms selected from N, O, and S and substituted with 0–3 $R^3$, $C_1$–$C_{10}$ alkyl substituted with 0–3 $R^3$, and cycloalkyl substituted with 0–3 $R^3$;

$R^3$ is independently selected at each occurrence from the group: =O, F, Cl, Br, I, —$CF_3$, —CN, —$CO_2R^4$, —C(=O)$R^4$, —C(=O)N($R^4$)$_2$, —$CH_2OR^4$, —OC(=O)$R^4$, —OC(=O)$OR^4$, —$OR^4$, —OC(=O)N($R^4$)$_2$, —$NR^4$C(=O)$R^4$, —$NR^4$C(=O)$OR^4$, —$NR^4$C(=O)N($R^4$)$_2$, —$NR^4SO_2$N($R^4$)$_2$, —$NR^4SO_2R^4$, —$SO_3H$, —$SO_2R^4$, —S(=O)$R^4$, —$SO_2$N($R^4$)$_2$, —N($R^4$)$_2$, —N($R^4$)$_3^+$, —NHC(=NH)$NHR^4$, —C(=NH)$NHR^4$, =$NOR^4$, —$NO_2$, —C(=O)$NHOR^4$, —C(=O)NHN($R^4$)$_2$, —$OCH_2C_2H$, 2-(1-morpholino)ethoxy, $C_1$–$C_{10}$ alkyl substituted with 0–3 $R^5$, $C_2$–$C_{10}$ alkenyl substituted with 0–3 $R^5$, $C_3$–$C_6$ cycloalkyl substituted with 0–3 $R^5$, aryl substituted with 0–3 $R^5$, and 5–10 membered heterocycle containing from 1–4 heteroatoms selected from N, O, and S and substituted with 0–3 $R^5$;

$R^4$ is independently selected at each occurrence from the group: H, $C_1$–$C_{10}$ alkyl substituted with 0–3 $R^5$, $C_2$–$C_{10}$ alkenyl substituted with 0–3 $R^5$, $C_3$–$C_6$ cycloalkyl substituted with 0–3 $R^5$, aryl substituted with 0–3 $R^5$, and 5–10 membered heterocycle containing from 1–4 heteroatoms selected from N, O, and S and substituted with 0–3 $R^5$; p2 $R^5$ is independently selected at each occurrence from the group: =O, F, Cl, Br, I, —$CF_3$, —CN, —$CO_2R^6$, —C(=O)$R^6$, —C(=O)N($R^6$)$_2$, —$CH_2OR^6$, —OC(=O)$R^6$, —OC(=O)O$R^6$, —O$R^6$, —OC(=O)N($R^6$)$_2$, —$NR^6$C(=O)$R^6$, —$NR^6$C(=O)O$R^6$, —$NR^6$C(=O)N($R^6$)$_2$, —$NR^6SO_2$N($R^6$)$_2$, —$NR^6SO_2R^6$, —$SO_3$H, —$SO_2R^6$, —S(=O)$R^6$, —$SO_2$N($R^6$)$_2$, —N($R^6$)$_2$, —N($R^6$)$_3^+$, —NHC(=NH)NH$R^6$, —C(=NH)NH$R^6$, =NO$R^6$, —NO$_2$, —C(=O)NHO$R^6$, —C(=O)NHN$R^6R^6$, —OCH$_2$C$_2$H, and phenyl;

provided that when $R^1$ is pyridyl-$R^3$, $R^3$ is C(O)N($R^4$)$_2$, and one $R_4$ is alkyl-($R^5$)$_2$, then $R^5$ at each occurrence is other than phenyl;

$R^6$ is independently selected at each occurrence from the group: H, and $C_1$–$C_6$ alkyl;

$R^7$ is selected from the group: hydrogen, hydroxy, aryl substituted with 0–3 $R^{14}$, and $C_1$–$C_{10}$ alkyl substituted with 0–3 $R^{15}$;

alternatively, $R^7$ and $R^8$ together form a 3–6 membered heterocycle containing from 1–4 heteroatoms selected from N, O, and S and substituted with 0–3 $R^{14}$;

$R^8$ and $R^9$ are independently selected from the group: hydrogen, hydroxyl, 5–10 membered heterocycle containing from 1–4 heteroatoms selected from N, O, and S and substituted with 0–3 $R^{14}$, $C_1$–$C_{10}$ alkyl substituted with 0–3 $R^{15}$, and cycloalkyl substituted with 0–3 $R^{15}$;

alternatively, $R^8$ and $R^9$ can be taken together to form a $C_3$–$C_6$ cycloalkyl substituted with 0–3 $R^{15}$;

$R^{10}$ is selected from the group: —COOH, phenyl substituted with 0–3 $R^{14}$, and 5–10 membered heterocycle containing from 1–4 heteroatoms selected from N, O, and S and substituted with 0–3 $R^{14}$;

$R^{11}$ and $R^{12}$ are independently selected at each occurrence from the group: H, —OH, —COOH, 5–10 membered heterocycle containing from 1–4 heteroatoms selected from N, O, and S and substituted with 0–3 $R^{14}$, $C_1$–$C_{10}$ alkyl substituted with 0–3 $R^{15}$, and cycloalkyl substituted with 0–3 $R^{15}$;

alternatively, $R^7$ and $R^{11}$ together form a 3–6 membered heterocycle containing from 1–4 heteroatoms selected from N, O, and S and substituted with 0–3 $R^{14}$ $R^{13}$ is —CH$_2$OH, or —CH$_2$CH$_2$OH;

m is 0–2;

$R^{14}$ is independently selected at each occurrence from the group: $C_1$–$C_5$ alkyl substituted with 0–3 $R^{15}$, $C_2$–$C_5$ alkenyl substituted with 0–3 $R^{15}$, $C_3$–$C_6$ cycloalkyl substituted with 0–3 $R^{15}$, aryl substituted with 0–3 $R^{15}$, and 5–10 membered heterocycle containing from 1–4 heteroatoms selected from N, O, and S and substituted with 0–3 $R^{15}$, F, Cl, Br, I, —$CF_3$, —CN, —$CO_2R^{16}$, —C(=O)$R^{16}$, —C(=O)N($R^{16}$)$_2$, —CH$_2$O$R^{16}$, —OC(=O)$R^{16}$, —OC(=O)O$R^{16}$, —O$R^{16}$, —OC(=O)N($R^{16}$)$_2$, —$NR^{16}$C(=O)$R^{16}$, —$NR^{16}$C(=O)O$R^{16}$, —$NR^{16}$C(=O)N($R^{16}$)$_2$, —$NR^{16}SO_2$N($R^{16}$)$_2$, —$NR^{16}SO_2R^{16}$, —$SO_3$H, —$SO_2R^{16}$, —$SO_2$N($R^{16}$)$_2$, —$PO_3H_2$, —NHC(=NH)NH$R^{16}$, —C(=NH)NH$R^{16}$, NO$_2$, —OCH$_2$CO$_2$H;

$R^{15}$ is independently selected at each occurrence from the group: =O, F, Cl, Br, I, —$CF_3$, —CN, —$CO_2R^{16}$, —C(=O)$R^{16}$, —C(=O)N($R^{16}$)$_2$, —CH$_2$O$R^{16}$, —OC(=O)$R^{16}$, —OC(=O)O$R^{16}$, —O$R^{16}$, —OC(=O)N($R^{16}$)$_2$, —$NR^{16}$C(=O)$R^{16}$, —$NR^{16}$C(=O)O$R^{16}$, —$NR^{16}$C(=O)N($R^{16}$)$_2$, —$NR^{16}SO_2$N($R^{16}$)$_2$, —$NR^{16}SO_2R^{16}$, —$SO_3$H, —$SO_2R^{16}$, —$SO_2$N($R^{16}$)$_2$, —$PO_3H_2$, —NHC(=NH)NH$R^{16}$, —C(=NH)NH$R^{16}$, NO$_2$, and —OCH$_2$CO$_2$H;

$R^{16}$ is independently selected at each occurrence from the group: hydrogen, and $C_1$–$C_6$ alkyl;

$A^1$ is selected from the group: P$R^{17}R^{18}R^{19}$ and As$R^{17}R^{18}R^{19}$;

$A^2$ and $A^3$ are independently selected at each occurrence from the group: P$R^{17}R^{18}$ and As$R^{17}R^{18}$;

$R^{17}$, $R^{18}$, and $R^{19}$ are independently selected at each occurrence from the group: aryl substituted with 0–3 $R^{20}$, 5–10 membered heterocycle containing from 1–4 heteroatoms selected from N, O, and S and substituted with 0–3 $R^{20}$, aralkyl substituted with 0–3 $R^{20}$, arylalkaryl substituted with 0–3 $R^{20}$, $C_1$–$C_{10}$ alkyl substituted with 0–3 $R^{21}$, and cycloalkyl substituted with 0–3 $R^{21}$;

W is a spacer group selected from the group: aryl substituted with 0–3 $R^{20}$, 5–10 membered heterocycle containing from 1–4 heteroatoms selected from N, O, and S and substituted with 0–3 $R^{20}$, aralkyl substituted with 0–3 $R^{20}$, $C_1$–$C_{10}$ alkyl substituted with 0–3 $R^{21}$, and cycloalkyl substituted with 0–3 $R^{21}$;

$R^{20}$ is independently selected at each occurrence from the group: $C_1$–$C_5$ alkyl substituted with 0–3 $R^{21}$, $C_2$–$C_5$ alkenyl substituted with 0–3 $R^{21}$, $C_3$–$C_6$ cycloalkyl substituted with 0–3 $R^{21}$, aryl substituted with 0–3 $R^{21}$, and 5–10 membered heterocycle containing from 1–4 heteroatoms selected from N, O, and S and substituted with 0–3 $R^{21}$, F, Cl, Br, I, —$CF_3$, —CN, —$CO_2R^{22}$, —C(=O)$R^{22}$, —C(=O)N($R^{22}$)$_2$, —CH$_2$O$R^{22}$, —OC(=O)$R^{22}$, —OC(=O)O$R^{22}$, —O$R^{22}$, —OC(=O)N($R^{22}$)$_2$, —$NR^{22}$C(=O)$R^{22}$, —$NR^{22}$C(=O)O$R^{22}$, —N($R^{22}$)$_2$, —N($R^{22}$)$_3^+$, —$NR^{22}$C(=O)N($R^{22}$)$_2$, —$NR^{22}SO_2$N($R^{22}$)$_2$, —$NR^{22}SO_2R^{22}$, —$SO_3$H, —$SO_2R^{22}$, —$SO_2$N($R^{22}$)$_2$, —$PO_3H_2$, —NHC(=NH)NH$R^{22}$, —C(=NH)NH$R^{22}$, NO$_2$, and —OCH$_2$CO$_2$H;

$R^{21}$ is independently selected at each occurrence from the group: =O, F, Cl, Br, I, —$CF_3$, —CN, —$CO_2R^{22}$, —C(=O)$R^{22}$, —C(=O)N($R^{22}$)$_2$, —CH$_2$O$R^{22}$, —OC(=O)$R^{22}$, —OC(=O)O$R^{22}$, —O$R^{22}$, —OC(=O)N($R^{22}$)$_2$, —$NR^{22}$C(=O)$R^{22}$, —$NR^{22}$C(=O)O$R^{22}$, —$NR^{22}$C(=O)N($R^{22}$)$_2$, —$NR^{22}SO_2$N($R^{22}$)$_2$, —$NR^{22}SO_2R^{22}$, —$SO_3$H, —$SO_2R^{22}$, —S(=O)$R^{22}$, —$SO_2$N($R^{22}$)$_2$, —N($R^{22}$)$_2$, —N($R^{22}$)$_3^+$, —$PO_3H_2$, —NHC(=NH)NH$R^{22}$, —C(=NH)NH$R^{22}$, =NO$R^{22}$, NO$_2$, —C(=O)NHO$R^{22}$, —C(=O)NHN($R^{22}$)$_2$, —OCH$_2$CO$_2$H;

$R^{22}$ is independently selected at each occurrence from the group: hydrogen and $C_1$–$C_6$ alkyl;

$X^1$ is independently selected at each occurrence from the group: C$R^{23}$ and N;

$X^2$ is independently selected at each occurrence from the group: C$R^{23}$, C$R^{23}R^{23}$, N, N$R^{23}$, O and S;

$X^3$ is independently selected at each occurrence from the group: C, C$R^{23}$, and N;

provided the total number of heteroatoms, $X^1$, $X^2$, and $X^3$ in each ring of the ligand, $L^3$, is 1, 2, 3, or 4;

Y is selected from the group: B$R^{23}$-, C$R^{23}$, (P=O), (P=S);

n is 0 or 1;

a, b, c, d, e and f indicate the positions of optional double bonds, provided that one of e and f is a double bond;

$R^{23}$ is independently selected at each occurrence from the group: H, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, $C_1$–$C_{10}$ alkoxy substituted with 0–3 $R^{24}$, $C_{3-13}$ carbocycle substituted with 0–3 $R^{24}$, and $R^{24}$;

alternatively, two $R^{23}$ may be taken together with the atom or atoms to which they are attached to form a fused aromatic substituted with 0–3 $R^{24}$, $C_{5-7}$ carbocyclic ring substituted with 0–3 $R^{24}$ or 5–7 membered heterocyclic ring containing from 1–4 heteroatoms selected from N, O, and S and substituted with 0–3 $R^{24}$;

$R^{24}$ is independently selected at each occurrence from the group: =O, F, Cl, Br, I, —$CF_3$, —CN, —$NO_2$, —$CO_2R^{25}$, —C(=O)$R^{25}$, —C(=O)N($R^{25}$)$_2$, —N($R^{25}$)$_3^+$, —$CH_2OR^{25}$, —OC(=O)$R^{25}$, —OC(=O)$OR^{25}$, —$OR^{25}$, —OC(=O)N($R^{25}$)$_2$, —$NR^{25}$C(=O)$R^{25}$, —$NR^{25}$C(=O)$OR^{25}$, —$NR^{25}$C(=O)N($R^{25}$)$_2$, —$NR^{25}SO_2$N($R^{25}$)$_2$, —$NR^{25}SO_2R^{25}$, —$SO_3H$, —$SO_2R^{25}$, —$SO_2$N($R^{25}$)$_2$, —N($R^{25}$)$_2$, —$OCH_2CO_2H$; and $R^{25}$ is independently selected at each occurrence from the group: hydrogen and $C_1$–$C_6$ alkyl;

$R^{26}$ and $R^{27}$ are independently selected from the group: H; $C_1$–$C_{10}$alkyl; —CN; —$CO_2R^{31}$; —C(=O)$R^{31}$; —C(=O)N($R^{31}$)$_2$; $C_2$–$C_{10}$ 1-alkene substituted with 0–3 $R^{30}$; $C_2$–$C_{10}$ 1-alkyne substituted with 0–3 $R^{30}$; aryl substituted with 0–3 $R^{30}$; unsaturated 5–10 membered heterocycle containing from 1–4 heteroatoms selected from N, O, and S and substituted with 0–3 $R^{30}$; and unsaturated $C_{3-13}$ carbocycle substituted with 0–3 $R^{30}$;

alternatively, $R^{26}$ and $R^{27}$, may be taken together with the divalent carbon radical to which they are attached to form:

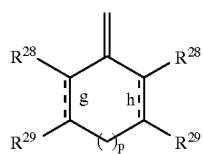

$R^{28}$ and $R^{29}$ are independently selected at each occurrence from the group: H; $R^{30}$; $C_1$–$C_{10}$ alkyl substituted with 0–3 $R^{30}$; $C_2$–$C_{10}$ alkenyl substituted with 0–3 $R^{30}$; $C_2$–$C_{10}$ alkynyl substituted with 0–3 $R^{30}$; aryl substituted with 0–3 $R^{30}$; 5–10 membered heterocycle containing from 1–4 heteroatoms selected from N, O, and S and substituted with 0–3 $R^{30}$; and $C_{3-13}$ carbocycle substituted with 0–3 $R^{30}$;

alternatively, $R^{28}$ and $R^{29}$ may be taken together to form a fused aromatic or 5–7 membered heterocyclic ring containing from 1–4 heteroatoms selected from N, O, and S;

g and h indicate the positions of optional double bonds and p is 0 or 1, $R^{30}$ is independently selected at each occurrence from the group: =O, F, Cl, Br, I, —$CF_3$, —CN, —$CO_2R^{31}$, —C(=O)$R^{31}$, —C(=O)N($R^{31}$)$_2$, —N($R^{31}$)$_3^+$, —$CH_2OR^{31}$, —OC(=O)$R^{31}$, —OC(=O)$OR^{31}$, —$OR^{31}$, —OC(=O)N($R^{31}$)$_2$, —$NR^{31}$C(=O)$R^{31}$, —$NR^{31}$C(=O)$OR^{31}$, —$NR^{31}$C(=O)N($R^{31}$)$_2$, —$NR^{31}SO_2$N($R^{31}$)$_2$, —$NR^{31}SO_2R^{31}$, —$SO_3H$, —$SO_2R^{31}$, —$SR^{31}$, —S(=O)$R^{31}$, —$SO_2$N($R^{31}$)$_2$, —N($R^{31}$)$_2$, —NHC(=NH)NHR$^{31}$, —C(=NH)NHR$^{31}$, =NOR$^{31}$, —C(=O)NHOR$^{31}$, —$OCH_2CO_2H$, 2-(1-morpholino)ethoxy; and $R^{31}$ is independently selected at each occurrence from the group: hydrogen, $C_1$–$C_6$ alkyl.

[6] In another preferred embodiment, the third ligand is selected from the group:

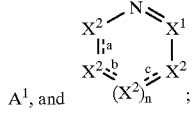

$A^1$, and $R^1$ is selected from the group: aryl substituted with 0–3 $R^3$, and 5–10 membered heterocycle containing from 1–4 heteroatoms selected from N, O, and S and substituted with 0–3 $R^3$;

$R^2$ is selected from the group: hydrogen, aryl substituted with 0–3 $R^3$, and 5–10 membered heterocycle containing from 1–4 heteroatoms selected from N, O, and S and substituted with 0–3 $R^3$;

$R^3$ is independently selected at each occurrence from the group: F, Cl, Br, I, —$CO_2R^4$, —C(=O)N($R^4$)$_2$, —$CH_2OR^4$, —OC(=O)$R^4$, —$OR^4$, —$NR^4$C(=O)$R^4$, —$NR^4SO_2R^4$, —$SO_3H$, —$SO_2$N($R^4$)$_2$, —N($R^4$)$_2$, —N($R^4$)$_3^+$, —$NO_2$, —$OCH_2CO_2H$, and $C_1$–$C_{10}$ alkyl substituted with 0–3 $R^5$;

$R^4$ is independently selected at each occurrence from the group: H, and $C_1$–$C_{10}$ alkyl substituted with 0–3 $R^5$;

$R^5$ is independently selected at each occurrence from the group: =O, F, Cl, Br, I, —$CO_2R^6$, —C(=O)N($R^6$)$_2$, —$CH_2OR^6$, —OC(=O)$R^6$, —$OR^6$, —$NR^6$C(=O)$R^6$, —$NR^6SO_2R^6$, —$SO_3H$, —$SO_2$N($R^6$)$_2$, —N($R^6$)$_2$, —N($R^6$)$_3^+$, —$NO_2$, —$OCH_2CO_2H$, and phenyl;

$R^7$ is selected from the group: hydrogen, and $C_1$–$C_{10}$ alkyl substituted with 0–3 $R^{15}$;

$R^8$ and $R^9$ are independently selected from the group: hydrogen, hydroxyl, and $C_1$–$C_{10}$ alkyl substituted with 0–3 $R^{15}$;

$R^{11}$ and $R^{12}$ are independently selected at each occurrence from the group: H, —OH, and $C_1$–$C_{10}$ alkyl substituted with 0–3 $R^{15}$;

m is 0–1;

$R^{14}$ is independently selected at each occurrence from the group: $C_1$–$C_5$ alkyl substituted with 0–3 $R^{15}$, F, Cl, Br, I, —$CO_2R^{16}$, —C(=O)N($R^{16}$)$_2$, —$CH_2OR^{16}$, —OC(=O)$R^{16}$, —$OR^{16}$, —$NR^{16}$C(=O)$R^{16}$, —$NR^{16}SO_2R^{16}$, —$SO_3H$, —$SO_2$N($R^{16}$)$_2$, —$PO_3H_2$, —$NO_2$, and —$OCH_2CO_2H$;

$R^{15}$ is independently selected at each occurrence from the group: =O, F, Cl, Br, I, —$CO_2R^{16}$, —C(=O)N($R^{16}$)$_2$, —$CH_2OR^{16}$, —OC(=O)$R^{16}$, —$OR^{16}$, —$NR^{16}$C(=O)$R^{16}$, —$NR^{16}SO_2R^{16}$, —$SO_3H$, —$SO_2$N($R^{16}$)$_2$, —$PO_3H_2$, and —$OCH_2CO_2H$;

$A^1$ is $PR^{17}R^{18}R^{19}$;

$R^{17}$, $R^{18}$, and $R^{19}$ are independently selected from the group: aryl substituted with 0–3 $R^{20}$, 5–10 membered heterocycle containing from 1–4 heteroatoms selected from N, O, and S and substituted with 0–3 $R^{20}$, and $C_1$–$C_{10}$ alkyl substituted with 0–3 $R^{21}$;

$R^{20}$ is independently selected at each occurrence from the group: $C_1$–$C_5$ alkyl substituted with 0–3 $R^{21}$, F, Cl, Br, I, —$CO_2R^{22}$, —C(=O)N($R^{22}$)$_2$, —$CH_2OR^{22}$, —OC(=O)$R^{22}$, —$OR^{22}$, —$NR^{22}$C(=O)$R^{22}$, —$NR^{22}SO_2R^{22}$, —$SO_3H$, —$SO_2N(R^{22})_2$, —N($R^{22}$)$_2$, —N($R^{22}$)$_3^+$, —$PO_3H_2$, and —$OCH_2CO_2H$;

$R^{21}$ is independently selected at each occurrence from the group: =O, F, Cl, Br, I, —$CO_2R^{22}$, —C(=O)N($R^{22}$)$_2$, —$CH_2OR^{22}$, —OC(=O)$R^{22}$, —$PO_3H_2$, —$OR^{22}$, —$NR^{22}$C(=O)$R^{22}$, —$NR^{22}SO_2R^{22}$, —$SO_3H$, —$SO_2N(R^{22})_2$, —N($R^{22}$)$_2$, —N($R^{22}$)$_3^+$, and —$OCH_2CO_2H$;

$X^2$ is independently selected at each occurrence from the group: $CR^{23}$, $CR^{23}R^{23}$, N, $NR^{23}$, and O;

provided the total number of heteroatoms, $X^1$, and $X^2$, is 1, 2, 3, or 4;

$R^{23}$ is independently selected at each occurrence from the group: H, $C_1$–$C_3$ alkyl substituted with 0–3 $R^{24}$, aryl substituted with 0–3 $R^{24}$, and $R^{24}$;

alternatively, two $R^{23}$ may be taken together with the atom or atoms to which they are attached to form a fused aromatic or a 5–7 membered heterocyclic ring containing from 1–4 heteroatoms selected from N, O, and S and substituted with 0–3 $R^{24}$; and $R^{24}$ is independently selected at each occurrence from the group: —$NO_2$, —$CO_2R^{25}$, —$OR^{25}$, —$SO_3H$, and —$OCH_2CO_2H$;

$R^{26}$ and $R^{27}$ are independently selected from the group: —$CO_2R^{31}$; $C_2$–$C_5$ 1-alkene substituted with 0–3 $R^{30}$; $C_2$–$C_5$ 1-alkyne substituted with 0–3 $R^{30}$; aryl substituted with 0–3 $R^{30}$; and unsaturated 5–10 membered heterocycle containing from 1–4 heteroatoms selected from N, O, and S and substituted with 0–3 $R^{30}$;

alternatively, $R^{26}$ and $R^{27}$, may be taken together with the divalent carbon radical to which they are attached to form:

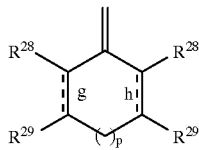

$R^{28}$ and $R^{29}$ may be independently selected from the group: H, and $R^{30}$;

alternatively, $R^{28}$, $R^{29}$ may be taken together to form a fused aromatic or a 5–7 membered heterocyclic ring containing from 1–4 heteroatoms selected from N, O, and S;

g and h indicate the positions of optional double bonds and p is 0 or 1, $R^{30}$ is independently selected at each occurrence from the group: —$CO_2R^{31}$, —C(=O)N($R^{31}$)$_2$, —$CH_2OR^{31}$, —OC(=O)$R^{31}$, —$OR^{34}$, —$SO_3H$, —N($R^{34}$)$_2$, and —$OCH_2CO_2H$; and, $R^{31}$ is independently selected at each occurrence from the group: hydrogen, and $C_1$–$C_3$ alkyl.

[7] In another even further preferred embodiment, the present invention provides novel kits wherein:

$R^1$ is selected from the group: aryl substituted with 0–1 $R^3$, and heterocycle substituted with 0–1 $R^3$, wherein said heterocycle is pyridine or phthalazine;

$R^2$ is selected from the group: hydrogen, and aryl substituted with 0–1 $R^3$;

$R^3$ is independently selected at each occurrence from the group: Cl, —$CO_2R^4$, —C(=O)N($R^4$)$_2$, —$OR^4$, —$SO_3H$, and —$NO_2$;

$R^4$ is independently selected at each occurrence from the group: H, and $C_1$–$C_{10}$ alkyl substituted with 0–2 $R^5$;

$R^5$ is selected from the group: —$CO_2R^6$, —$OR^6$, and phenyl;

$R^6$ is independently selected from the group: H, and methyl;

$R^7$, $R^8$, and $R^9$ are hydrogen;

$R^{10}$ is selected from the group: —COOH, and 2-hydroxyphenyl;

m is 0–1, provided that when $R^{10}$ is —COOH, m is 1;

$R^{11}$, $R^{12}$, and $R^{13}$ are —$CH_2OH$;

$A^1$ is $PR^{17}R^{18}R^{19}$;

$R^{17}$, $R^{18}$, and $R^{19}$ are independently selected from the group: aryl substituted with 0–1 $R^{20}$, 5–10 membered heterocycle containing from 1–4 heteroatoms selected from N, O, and S and substituted with 0–1 $R^{20}$, and $C_1$–$C_3$ alkyl substituted with 0–1 $R^{21}$;

$R^{20}$ is independently selected at each occurrence from the group: —$CO_2R^{22}$, —$OR^{22}$, and —$SO_3H$;

$R^{21}$ is selected from the group: —$CO_2R^{22}$, and —$OR^{22}$;

$R^{22}$ is independently selected from the group: H, and methyl;

$X^1$ is CH;

$X^2$ is independently selected at each occurrence from the group: CH, and NH, provided only one $X^2$ is NH;

$R^{26}$ is selected from the group: —$CO_2R^{31}$; $C_2$–$C_3$ 1-alkene substituted with 0–1 $R^{30}$; aryl substituted with 0–1 $R^{30}$; unsaturated 5–10 membered heterocycle containing from 1–4 heteroatoms selected from N, O, and S and substituted with 0–1 $R^{30}$;

$R^{27}$ is H;

$R^{30}$ is independently selected at each occurrence from the group: —$CO_2R^{31}$, —$OR^{31}$, —$SO_3H$, and —N($R^{31}$)$_2$; and $R^{31}$ is independently selected at each occurrence from the group: hydrogen, and methyl.

[8] In a still further preferred embodiment, the novel kit, further comprises: a reducing agent.

[9] In a more preferred embodiment, the reducing agent is Sn(II).

[10] In another still further preferred embodiment, the first ligand, the second ligand, and the third ligand are contained in the same vial.

Another embodiment of this invention is a method of imaging the heart in a mammal, comprising (i) administering an effective amount of one of the present radiopharmaceuticals and (ii) imaging said mammal using gamma scintigraphy.

Another embodiment of this invention is a method of imaging the brain in a mammal, comprising (i) administering an effective amount one of the present radiopharmaceuticals and (ii) imaging said mammal using gamma scintigraphy.

Another embodiment of this invention is a method of imaging the lungs in a mammal, comprising (i) administering an effective amount one of the present radiopharmaceuticals and (ii) imaging said mammal using gamma scintigraphy.

Another embodiment of this invention is a method of imaging the hepatobiliary system in a mammal, comprising (i) administering an effective amount of one of the present radiopharmaceuticals and (ii) imaging said mammal using gamma scintigraphy.

Another embodiment of this invention is a method of imaging the kidneys in a mammal, comprising (i) administering an effective amount of one of the present radiopharmaceuticals and (ii) imaging said mammal using gamma scintigraphy.

DEFINITIONS

The following abbreviations are used herein:

HYPY=2-hydrazinopyridine,

HYNICamide=6-hydrazinonicotinamide,

HYNIC-DMA=6-hydrazino-N,N-dimethylnicotinamide,

HYNIC-Gly-OMe=6-hydrazinonicotinylglycine methyl ester,

HYNIC-D-Phe-OMe=6-hydrazinonicotinyl-D-phenylalanine methyl ester,

DPH=N,N-diphenylhydrazine,

PHY=phenylhydrazine,

HYLA=hydralazine,

4-Cl-PHY=4-chlorophenylhydrazine,

4-$NO_2$-PHY=4-nitrophenylhydrazine, hbtris=2-(2-hydroxybenzyl)amino-2-hydroxymethyl-1,3-propanediol, TPPTS=tris(3-sulfonatophenyl)phosphine, TPPMS=(3-sulfonatophenyl)diphenylphosphine, and TFP=tris(2-furanyl)phosphine.

When any variable occurs more than one time in any constituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —$N(R^{53})_2$, each of the two $R^{53}$ substituents on N is independently selected from the defined list of possible $R^{53}$. Combinations of substituents and/or variables are permissible only if such combinations result in stable compounds.

By "stable compound" or "stable structure" is meant herein a compound that is sufficiently robust to survive isolation to a useful degree of purity from a reaction mixture, and formulation into an efficacious diagnostic agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla., 1984, as any substance which yields ions, other than hydrogen or hydroxyl ions.

As used herein, "alkyl" is intended to include both branched and straight-chain saturated aliphatic hydrocarbon groups having the specified number of carbon atoms, examples of which include methyl, ethyl, n-propyl, i-propyl, n-butyl, i-butyl, s-butyl, and t-butyl; "cycloalkyl" or "carbocycle" is intended to include saturated and partially unsaturated ring groups, including any stable 3- to 10-membered monocyclic or 7-13-membered bi- or poly-cyclic ring system, such as cyclopropyl, cyclobutyl, cyclopentyl, cyclohexyl, cycloheptyl, cyclooctyl, and adamantyl; "bicycloalkyl" is intended to include saturated bicyclic ring groups such as [3.3.0]bicyclooctane, [4.3.0]bicyclononane, [4.4.0]bicyclodecane (decalin), and [2.2.2]bicyclooctane.

As used herein, the term "alkene" or "alkenyl" is intended to include both branched and straight-chain groups of the formula $C_nH_{2n-1}$ having the specified number of carbon atoms, such as ethenyl and propenyl.

As used herein, the term "alkyne" or "alkynyl" is intended to include both branched and straight-chain groups of the formula $C_nH_{2n-3}$ having the specified number of carbon atoms, such as ethynyl and propynyl.

As used herein, "aryl" or "aromatic residue" is intended to mean phenyl or naphthyl, which when substituted, the substitution can be at any position.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its nendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1, 2, 3, or 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoouinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidlnyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoauinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthreniyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimldazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein to describe the substituents $R^{26}$ and $R^{27}$, the term "unsaturated carbocycle" means a carbocycle that has at least one multiple bond, that one multiple bond being between the carbon atom attached to the divalent carbon radical specified in the formula of the stable hydrazone moiety and an adjacent carbon atom, examples of which include cyclopentene, cyclohexene, and 1,4-cyclohexadiene.

As used herein to describe the substituents $R^{26}$ and $R^{27}$, the term "unsaturated heterocycle" means a heterocycle that has at least one multiple bond, that one multiple bond being between the carbon atom attached to the divalent carbon radical specified in the formula of the stable hydrazone moiety and an adjacent carbon atom. An aromatic heterocycle is considered an unsaturated heterocycle.

As used herein, the term "alkaryl" means an aryl group bearing an alkyl group of 1–10 carbon atoms, such as toluenyl; the term "aralkyl" means an alkyl group of 1–10 carbon atoms bearing an aryl group, such as benzyl; the term "arylalkaryl" means an aryl group bearing an alkyl group of 1–10 carbon atoms bearing an aryl group, such as phenylmethylphenyl; and the term "heterocycloalkyl" means an alkyl group of 1–10 carbon atoms bearing a heterocycle, such as pyridylmethyl or 2-imidazolylmethyl.

A "reducing agent" is a compound that reacts with the radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

The term "ligand" as used herein refers to a molecule or group of atoms that bonds to a metal ion through one of more of its constituent atoms, termed donor atoms.

The term "donor atom" refers to the atom directly attached to a metal by a chemical bond.

The term "ligand precursor" as used herein refers to a ligand in which one or more of its donor atoms bear a protecting group. A hydrazone is a precursor for a hydrazine ligand.

A "diagnostic kit" or "kit" comprises a collection of components, termed the formulation, in one or more vials which are used by the practicing end user in a clinical or pharmacy setting to synthesize the radiopharmaceutical. The kit provides all the requisite components to synthesize and use the radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

A "buffer" is a compound that is used to control the pH of the kit during its manufacture and during the synthesis of the radiopharmaceutical.

A "lyophilization aid" is a component that has favorable physical properties for lyophilization, such as the glass transition temperature, and is added to the diagnostic kit to improve the physical properties of the combination of all the components of the kit for lyophilization.

A "stabilization aid" is a component that is added to the radiopharmaceutical or to the diagnostic kit either to stabilize the radiopharmaceutical once it is synthesized or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid" is a component that improves the solubility of one or more other components in the medium required for the synthesis of the radiopharmaceutical.

A "bacteriostat" is a component that inhibits the growth of bacteria in the diagnostic kit either during its storage before use of after the kit is used to synthesize the radiopharmaceutical.

The term "pharmaceutically acceptable" as used herein means that a component is sufficiently sterile, apyrogenic and of such a chemical and physical form to be safely administered to a mammal, preferably a human.

The radiopharmaceuticals of the present invention have the formula $ML^1L^2L^3$, wherein M represents the transition metal radionuclide and $L^1$, $L^2$ and $L^3$ represent three different ligands that are coordinated to the metal radionuclide. These complexes are thus comprised of a ternary ligand system with a 1:1:1 ligand stoichiometry. These complexes can be formed in high specific activity, have high stability in vitro, and their chemical and biological properties can be readily tailored to the desired radiopharmaceutical application by the selection of the ligands $L^1$, $L^2$ and $L^3$.

The transition metal radionuclide is selected from the group: technetium-99m, rhenium-186 and rhenium-188. For diagnostic purposes Tc-99m is the preferred isotope. Its 6 hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy, however, they also emit high energy beta particles that are more damaging to living tissues. These beta particle emissions can be utilized for therapeutic purposes, for example, cancer radiotherapy.

The coordination sphere of the radionuclide includes all the ligands or groups bound to the radionuclide. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If one ligand does not provide all of the atoms necessary to stabilize the metal radionuclide by completing its coordination sphere, the coordination sphere is completed by donor atoms from other ligands, termed co-ligands, which can also be either terminal or chelating.

The radiopharmaceuticals of the present invention are comprised of three ligands, $L^1$, $L^2$ and $L^3$. The ligand $L^1$ is a hydrazido or diazenido ligand having the formula =N—NR$^1$R$^2$ or =N$^+$=NR$^1$ and results from the coordination of a hydrazine to the metal. A diazenido group can be either terminal (only one atom of the group is bound to the radionuclide) or chelating. In order to have a chelating diazenido group at least one other atom of the group must also be bound to the radionuclide. The ligand $L^2$ is comprised of two or more hard donor atoms such as oxygen and amine nitrogen (sp$^3$ hybridized). The donor atoms occupy at least two of the sites in the coordination sphere of the radionuclide metal. The ligand $L^3$ is comprised of one to three soft donor atoms selected from the group: phosphine phosphorus, arsine arsenic, imine nitrogen (sp$^2$ hybridized), sulfur (sp$^2$ hybridized) and carbon (sp hybridized); atoms which have pi-acid character. Ligands $L^3$ can be monodentate, bidentate or tridentate, the denticity is defined by the number of donor atoms in the ligand.

The chemical and physical properties of the radiopharmaceuticals of the present invention, such as their charge and lipophilicity, can be modified by the choice of substituents on the ligands, $L^1$, $L^2$ and $L^3$. Substituents that increase the lipophilicity of the complexes are comprised of predominantly carbon-carbon bonds, for example, alkyl, aryl, alkenyl, alkynyl and cycloalkyl groups. Substituents that increase the hydrophilicity of the complexes are comprised predominantly of nitrogen or oxygen heteroatoms, for example, carboxyl, hydroxyl, sulfonate, phosphonate, as well as others. Substituents that effect the charge of the complexes are comprised of groups that are charged under physiological conditions, for example, carboxyl, sulfonate, phosphonate, and ammonium.

The lipophilicity and charge of radiopharmaceuticals determine to a large extent their biological properties, such as the organs in which they concentrate, the rate of clearance from the blood and the route of excretion from the body. For example, Deutsch et. al., U.S. Pat. No. 4,387,087 describes cationic, binary ligand complexes with a lipophilicity measured by the 1-octanol-water partition coefficient of >0.05 that are useful as hepatobiliary and myocardial imaging agents. Bergstein et. al., U.S. Pat. No. 5,279,811 describes a series of neutral and lipophilic complexes of technetium-99m useful as brain imaging agents. Also, the relationship between lipophilicity, as measured by HPLC retention time, and route of excretion has been described by Nunn in Nucl. Med. Biol., 1989, 16, 187–190, herein incorporated by reference in its entirety, for a series of Tc-99m labeled iminodiacetic acid derivatives. The ternary ligand complexes of the present invention provide three independent means for affecting their lipophilicity and charge by the choice of the substituents on the three ligands.

The ligands $L^1$ in their uncoordinated or "free ligand" state can be obtained for use in the synthesis of the radiopharmaceuticals of the present invention from commercial sources in the form of a hydrazine or hydrazine derivative or acid salt thereof. In addition, methods for synthesizing hydrazines and their derivatives are well known to those skilled in the art. A number of synthesis methods can be found in March, Advanced Organic Chemistry, 3rd edition, Wiley-Interscience, herein incorporated by reference. Preferred ligands $L^1$ are hydrazines wherein the substituent $R^1$ is aryl or heterocycle.

Protected hydrazines or hydrazine derivatives can also be synthesized in the form of a hydrazone. The hydrazone protecting group can be removed either prior to or concomitantly with the synthesis of the radiopharmaceuticals. Exemplary hydrazones include aldehyde or ketone hydrazones having substituents, designated $R^{26}$ and $R^{27}$ in this application, selected from hydrogen, alkyl, aryl and heterocycle, which can be conveniently synthesized by condensation of the aldehyde or ketone with the hydrazine. When one of the substituents $R^{26}$ and $R^{27}$ is selected from the group: nitrile, carboxylic acids, carboxylic acid esters, carboxamides, 1-alkenes, 1-alkynes, aryl, unsaturated heterocycle, and unsaturated carbocycle; or the two substituents $R^{26}$ and $R^{27}$ are taken together to form a ring system, the hydrazones have improved stability. The substituents in the group serve to stabilize the hydrazone by providing a conjugated pi-electron system either as a carbon-carbon double bond or an aromatic ring. Enhanced stability can also be provided by the chelate effect if the substituents are taken together in a ring system. The synthesis and use of hydrazine-derivatized biologically active molecules having these preferred hydrazones with enhanced stability as the protecting group for the hydrazines are described in co-pending U.S. Ser. No. 08/476,296, herein incorporated by reference.

The ligands, $L^2$, in their uncoordinated or "free ligand" state are functionalized aminoalcohols or aminocarboxylates having at least one amine nitrogen donor atom. At least one additional nitrogen or oxygen donor atom must be present in the ligand in substituents $R^7$ through $R^{13}$. A large number of ligands $L^2$ can be obtained from commercial sources. Examples of ligands, $L^2$, include the series of functionalized aminocarboxylates disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields and higher specific activity of the radiopharmaceuticals of the present invention. The preferred ligands $L^2$ are functionalized aminocarboxylates that are derivatives of glycine; the most preferred is tricine (tris(hydroxymethyl) methylglycine).

The ligands $L^3$ that are comprised of phosphine or arsine donor atoms are trisubstituted phosphines, trisubstituted arsines, tetrasubstituted diphosphines and tetrasubstituted diarsines. The ligands $L^3$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources or can be synthesized by a variety of means known to those skilled in the art. A number of methods for synthesizing phosphines can be found in Kosolapoff and Maier, *Organic Phosphorus Compounds*: Wiley-Interscience: New York, 1972; Vol. 1. Isonitriles can be synthesized as described in European Patent 0107734 and in U.S. Pat. No. 4,988,827, herein incorporated by reference.

Preferred ligands $L^3$ are trisubstituted phosphines and unsaturated or aromatic 5 or 6 membered heterocycles. References for the synthesis of specific preferred ligands can be obtained as follows: Tris(3-sulfonatophenyl)phosphine, sodium salt (TPPTS) was synthesized as described in Bartik et. al., Inorg. Chem., 1992, 31, 2667. Bis(3-sulfonatophenyl) phenylphosphine, sodium salt (TPPDS) and (3-sulfonatophenyl)diphenylphosphine, sodium salt (TPPMS) were synthesized as described in Kuntz, E., U.S. Pat. No. 4,248,802. We have disclosed in co-pending U.S. Ser. No. 08/415,908, and U.S. Ser. No. 60/013360 and 08/646,886, the disclosures of which are herein incorporated by reference in their entirety, that radiopharmaceuticals comprised of a biologically active molecule, Q, bearing a chelator or metal bonding unit and one or more ancillary or co-ligands $L^3$ are more stable compared to radiopharmaceuticals that are not comprised of one or more ancillary ligands, $L^3$; that is, they have a minimal number of isomeric forms, the relative ratios of which do not change significantly with time, and that remain substantially intact upon dilution. The radiopharmaceuticals of the present invention differ from those claimed in these co-pending applications by the absence of the biologically active group, Q, on ligand $L^1$.

The radiopharmaceuticals of the present invention can be easily prepared by admixing a salt of a radionuclide, a ligand $L^1$ as a hydrazine or hydrazone, a ligand $L^2$, a ligand $L^3$, and a reducing agent, in an aqueous solution at temperatures from 0 to 100° C. When the ligand, $L^1$, is a hydrazone, then it must first be converted to a hydrazine, which may or may not be protonated, prior to complexation with the metal radionuclide. The conversion of the hydrazone group to the hydrazine can occur either prior to reaction with the radionuclide or in the presence of the radionuclide In the latter case, the pH of the reaction mixture must be neutral or acidic.

Alternatively, the radiopharmaceuticals of the present invention can be prepared by first admixing a salt of a radionuclide, a ligand $L^2$, and a reducing agent in an aqueous solution at temperatures from 0 to 100° C. to form an intermediate radionuclide complex with the ligand $L^2$ then adding the ligands $L^1$ and $L^3$ and reacting further at temperatures from 0 to 100° C.

Alternatively, the radiopharmaceuticals of the present invention can be prepared by first admixing a salt of a radionuclide, a ligand $L^1$ and a ligand $L^2$, and a reducing agent in an aqueous solution at temperatures from 0 to 100° C. to form an intermediate radionuclide complex, and then adding a ligand $L^3$ and reacting further at temperatures from 0 to 100° C.

The total time of preparation will vary depending on the identity of the radionuclide, the identities and amounts of the reactants and the procedure used for the preparation. The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the ligand $L^1$ used to prepare the radiopharmaceuticals of the present invention can range from 0.01 µg to 10 mg, or more preferably from 0.5 µg to 200 µg. The amount of the ligand $L^2$ used can range from 0.1 mg to 1 g, or more preferably from 1 mg to 100 mg. The amounts of the ligand $L^3$ used can range from 0.001 mg to 1 g, or more preferably from 0.01 mg to 10 mg. The amount used will be dictated by the amounts of the other reactants and the identity of the radiopharmaceuticals of the present invention to be prepared.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg. The use of a reducing agent can be omitted if the ligand $L^3$ can serve as both a reducing agent and a ligand. Ligands, $L^3$, that can serve both functions are those comprised of phosphorus or arsenic donor atoms.

Another aspect of the present invention are diagnostic kits for the preparation of the radiopharmaceuticals useful as imaging agents. Diagnostic kits of the present invention comprise one or more vials containing the sterile, nonpyrogenic, formulation comprised of a predetermined amount of the ligands $L^1$, $L^2$ and $L^3$ and optionally other components such as reducing agents, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The one or more vials that contain all or part of the formulation can independently be in the form of a sterile solution or a lyophilized solid.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the United States Pharmacopoeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monooleate, polysorbates, poly(oxyethylene)poly(oxypropylene)poly (oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

The amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the radiopharmaceutical and have a high degree of certainty that the radiopharmaceutical can be safely injected into a patient and will provide diagnostic information about the disease state of that patient.

The radiopharmaceuticals are administered by intravenous injection, usually in saline solution, at a dose of 1 to 100 mCi per 70 kg body weight, or preferably at a dose of 5 to 50 mCi. Imaging is performed using known procedures. Detailed procedures for imaging various organs in the body, including the heart, brain, lungs, liver and kidneys, and diagnosing diseases affecting those organs from the images can be found in Early and Sodee, *Principles and Practice of Nuclear Medicine*, 2nd edition, Mosby-Year Book, Inc., 1995, herein incorporated by reference.

Other features of the invention will become apparent in the course of the following descriptions of exemplary embodiments which are given for illustration of the invention and are not intended to be limiting thereof.

EXAMPLES

Starting materials used in the synthesis of the radiopharmaceuticals of the present invention described in this section were obtained from commercial sources and used as received. (The names of the ligands in the complexes below refer to the uncoordinated or free ligand form.)

Example 1

Synthesis of [$^{99m}$Tc(HYPY) (tricine) (TPPTS)]

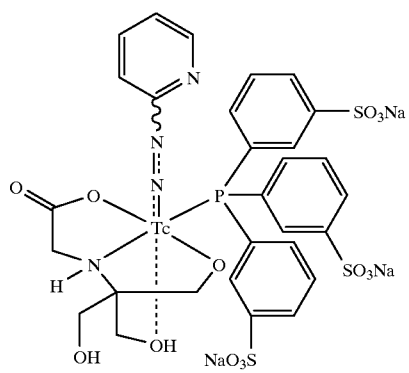

To a 10 mL vial was added 0.4 mL of tricine solution (40 mg) in $H_2O$, followed by 25 μL of 2-hydrazinopyridine hydrochloride solution (25 μg) in $H_2O$, 0.3 mL of $^{99m}TcO_4^-$ solution (30 mCi), 0.2 mL of TPPTS solution (1 mg) in $H_2O$ and 25 μl of $SnCl_2.2H_2O$ solution (50 μg) in 0.1N HCl. The reaction mixture was heated at 80° C. for 30 min, and was then analyzed by radio-HPLC (method 1). The radiolabeling yield was 95%. $R_t$=5.3 and 5.6 min.

Example 2

Synthesis of [$^{99m}$Tc(HYPY) (tricine) (TPPMS)]

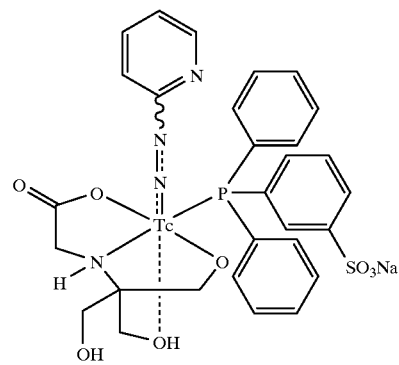

To a 10 mL vial was added 0.4 mL of tricine solution (40 mg) in 25 mM adipic acid buffer (pH 5), followed by 25 μL of 2-hydrazinopyridine hydrochloride solution (25 μg) in 25 mM adipic acid buffer (pH 5), 0.5 mL of $^{99m}TcO_4^-$ solution (50 mCi), 0.2 mL of TPPMS solution (2 mg) in 25 mM adipic acid buffer (pH 5) and 25 μl of $SnCl_2.2H_2O$ solution (50 μg) in 0.1N HCl. The reaction mixture was heated at 100° C. for 15 min, and was then analyzed by radio-HPLC (method 1). The radiolabeling yield was 90%. $R_t$=16.8 min.

Example 3

Synthesis of [$^{99m}$Tc(HYPY) (tricine) (imidazole)]

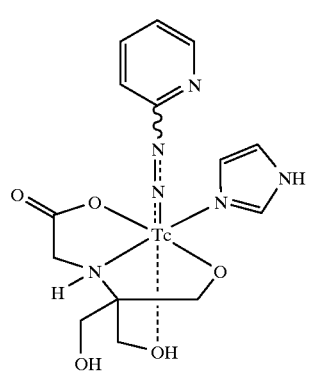

To a 10 mL vial was added 0.4 mL of tricine solution (40 mg) in $H_2O$, followed by 0.2 mL of 2-hydrazinopyridine hydrochloride solution (20 μg), 0.25 mL of $^{99m}TcO_4^-$ solution (50 mCi), 0.2 mL of imidazole solution (2 mg) in $H_2O$ and 25 μl of $SnCl_2.2H_2O$ solution (25 μg) in 0.1N HCl. The reaction mixture was heated at 80° C. for 30 min, and was then analyzed by radio-HPLC (method 2). The radiolabeling yield was 64%. $R_t$=7.1 min.

Example 4

Synthesis of [$^{99m}$Tc (2HYPY) (tricine) (pyridine)]

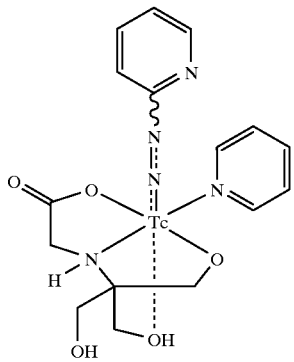

To a 10 mL vial was added 0.4 mL of tricine solution (40 mg) in H$_2$O, followed by 0.2 mL of 2-hydrazinopyridine hydrochloride solution (20 µg), 0.25 mL of $^{99m}$TcO$_4$- solution (50 mCi), 0.2 mL of pyridine hydrochloride solution (2 mg) in H$_2$O and 25 µl of SnCl$_2$.2H$_2$O solution (25 µg) in 0.1N HCl. The reaction mixture was heated at 80° C. for 30 min, and was then analyzed by radio-HPLC (method 2). The radiolabeling yield was 76%. R$_t$=7.3 min.

Example 5

Synthesis of [$^{99m}$Tc (HYPY) (tricine) (TFP)]

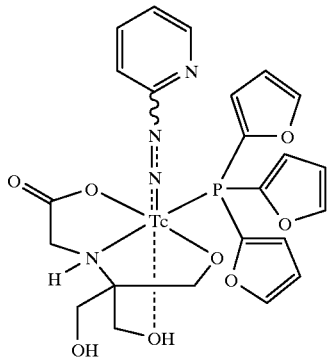

To a 10 mL vial was added 0.4 mL of tricine solution (40 mg) in H$_2$O, followed by 0.2 mL of 2-hydrazinopyridine hydrochloride solution (20 µg), 0.25 mL of $^{99m}$TcO$_4$- solution (50 mCi), 0.2 mL of tris(2-furanyl)phosphine solution (2 mg) in EtOH and 25 µl of SnCl$_2$.2H$_2$O solution (25 µg) in 0.1NHCl. The reaction mixture was heated at 80° C. for 30 min, and was then analyzed by radio-HPLC (method 2). The radiolabeling yield was 93%. R$_t$=18.8 min.

Example 6

Synthesis of [$^{99m}$Tc(HYPY) (tricine) (PPh$_3$)]

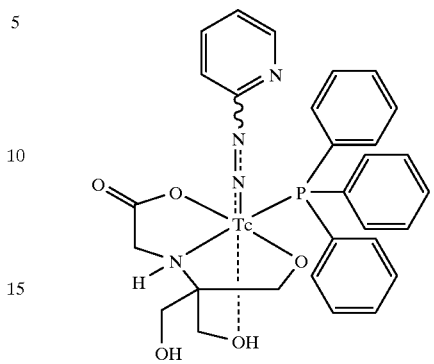

To a clean 10 mL vial was added 0.3 mL of tricine solution (100 mg/mL in H$_2$O), followed by 0.1 mL of 2-hydrazinopyridine hydrochloride solution (100 µg/mL) in H$_2$O, 0.3 mL of $^{99m}$TcO$_4$- solution (100 mCi/mL) in saline, 1.0 mL of triphenyliphosphine (PPh$_3$) solution (2 mg/mL) in absolute ethanol, and 20 µl of SnCl$_2$.2H$_2$O solution (1.0 mg/mL) in 0.1N HCl. The reaction mixture was heat ed at 50° C. for 30 min, and was then analyzed by radio-HPLC (method 1). The yield was 95%. R$_t$22.4 min.

Example 7

Synthesis of [$^{99m}$Tc (HYNICamide) (tricine) (TPPTS)]

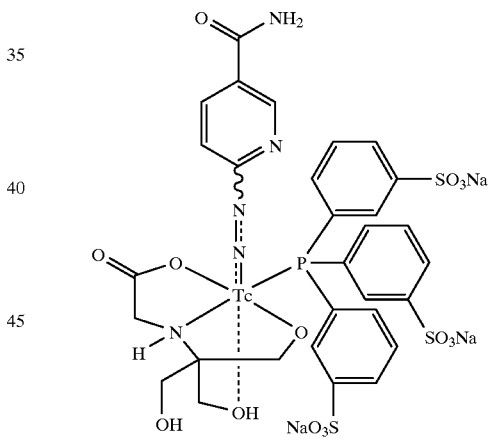

Part A: Synthesis of Succinimidyl 6-(2-sulfobenzaldehydehydrazono)nicotinate Sodium Salt To a suspension of 6-hydrazinonicotinic acid (1.00 g, 6.5 mmol) in DMF (40 ml) was added benzaldehyde (0.70 ml, 6.9 mmol), and the reaction mixture was allowed to stir at room temperature for 3 hours. To the homogeneous reaction mixture was added N-hydroxysuccinimide (752 mg, 6.5 mmol) and DCC (3.00 ml, 13.4 mmol), and the reaction mixture was allowed to stir at room temperature for 18 hours. The reaction mixture was filtered, concentrated, diluted with EtOAc (50 ml), and the mixture was heated at reflux for 1 hour. Filtration of the hot mixture provided the title compound (1.78 g, 81%) as a pale yellow powder. This material was used without further purification. $^1$H NMR (D$_6$-DMSO) 11.86 (s, NH), 8.82 (dd, Py-H), 8.20 (dd, Py-H), 8.20 (s, =CH), 7.75 (dd, 2 Ar-H), 7.43 (m, Py-H & 3 Ar-H), 2.89 (s, 2 CH$_2$); DCI(NH$_3$)-MS: [M+H]=339.1084 (Calcd for C$_{17}$H$_{15}$N$_4$O$_4$=339.1093).

Part B: Synthesis of 6-(2-sulfobenzaldehydehydrazono) nicotinamide Sodium Salt

To a solution of succinimidyl 6-(2-sulfobenzaldehydehydrazono)nicotinate sodium salt (88.1 mg, 0.2 mmol) in DMF (1.0 mL) was added ammonium acetate (30 mg, 0.4 mmol). The reaction mixture was stirred at room temperature for 5–6 hour. DMF was removed by rotary evaporation. The residue was triturated with ethyl acetate (5 mL). The precipitate was collected by filtration, washed with ethyl acetate, and dried in vacuo to give a pale yellow solid. The yield was 70 mg. Mass spectrum (high resolution FAB-MS in glycerol matrix): M/e= 321.065752 (calculated mass=321.065224).

Part C: Synthesis of [$^{99m}$Tc(HYNICamide) (tricine) (TPPTS)]

To a 10 mL vial was added 0.4 mL of tricine solution (40 mg) in H$_2$O, followed by 0.2 mL of 6-(2-sulfobenzaldehydehydrazono)nicotinamide sodium salt (20 µg) in H$_2$O, 0.4 mL of $^{99m}$TcO$_4^-$ solution (40 mCi), 0.1 mL of TPPTS solution (1 mg) in H$_2$O and 10 µl of SnCl$_2$.2H$_2$O solution (100 µg in 0.1N HCl). The reaction mixture was heated at 80° C. for 20 min, and was then analyzed by radio-HPLC (method 1). The radiolabeling yield was 82%. R$_t$=6.6 min.

Example 8

Synthesis of [$^{99m}$Tc (HYNIC-DMA) (tricine) (TPPTS)]

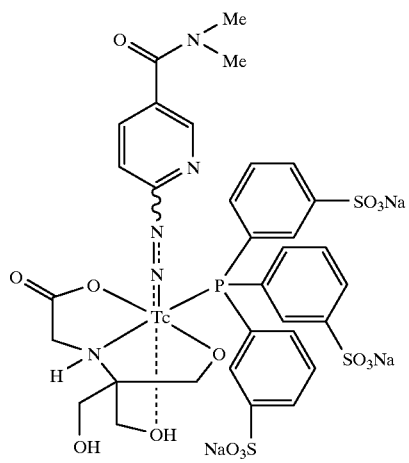

Part A: Synthesis of N,N-Dimethyl-6-(2-sulfobenzaldehydehydrazono)nicotinamide Sodium Salt To a solution of succinimidyl 6-(2-sulfobenzaldehydehydrazono)nicotinate sodium salt in DMF (50 ml) was added Me$_2$NH/H$_2$O (1 ml), and the reaction mixture was allowed to stir at RT for 9 days. The reaction mixture was concentrated, and triturated with hot EtOAc. The residue was triturated a second time with hot MeOH/EtOAc (1:2 ratio), cooled to RT, and collected by vacuum filtration to provide the title compound (742 mg, 88%) as a pale yellow powder; $^1$H NMR (D$_6$-DMSO) 11.26 (br s, NH), 9.00 (s, 1H), 8.21 (d, 1H), 8.01 (dd, 1H), 7.77 (dd, 1H), 7.70 (dd, 1H), 7.30 (m, 3H), 4.11 (q, OH from MeOH), 3.16 (d, Me from MeOH), 2.99 (s, NMe$_2$); FAB (NBA)-MS: [M+H]=371.0775 (Calcd for C$_{15}$H$_{16}$N$_4$O$_4$SNa=371.0790).

Part B: Synthesis of [$^{99m}$Tc(HYNIC-DMA) (tricine) (TPPTS)]

To a 10 mL vial was added 0.4 mL of tricine solution (40 mg) in H$_2$O, followed by 0.2 mL of N,N-Dimethyl-6-(2-sulfobenzaldehydehydrazono)nicotinamide sodium salt solution (20 µg), 0.4 mL of $^{99m}$TcO$_4^-$ solution (50 mCi) and 10 µl of SnCl$_2$.2H$_2$O solution (100 µg) in 0.1N HCl. The reaction mixture was heated at 80° C. for 15 min. To the reaction mixture above was added 0.2 mL of TPPTS solution (2 mg) in H$_2$O . The reaction mixture was heated for another 15 min at 80° C., and was then analyzed by radio-HPLC (method 1). The radiolabeling yield was 96%. R$_t$=7.0 and 7.3 min.

Example 9

Synthesis of [$^{99m}$Tc(HYNIC-Gly-OMe) (tricine) (TPPTS)]

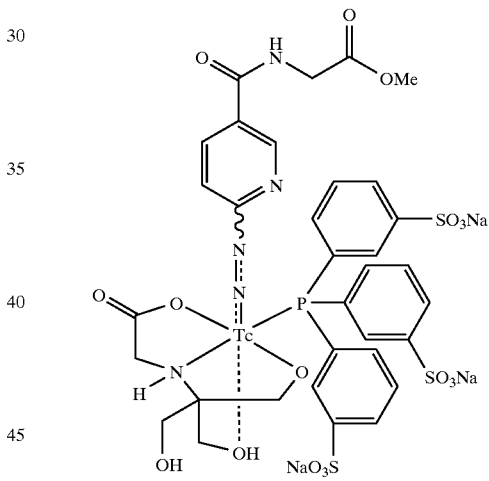

Part A: Synthesis of N-(Carbomethoxymethyl)-6-(2-sulfobenzaldehydehydrazono)nicotinamide Sodium Salt To a solution of 285 mg (2.27 mmol) of glycine methyl ester and 1.0 g (2.27 mmol) of succinimidyl 6-(2-sulfobenzaldehydehydrazono)nicotinate sodium salt in DMF (50 ml) was added Et$_3$N (0.65 ml), and the reaction mixture was allowed to stir at RT for 4 days. The reaction mixture was filtered, concentrated, and triturated with hot EtOAc. The residue was triturated a second time with hot MeOH/EtOAc, cooled to RT, and collected by vacuum filtration to provide the title compound (593 mg, 63%) as a pale yellow powder; $^1$H NMR (D$_6$-DMSO) 11.44 (br s, NH), 9.04 (s, 1H), 8.86 (br t, NH), 8.63 (d, 1H), 8.05 (dt, 2H), 7.78 (dd, 1H), 7.30 (m, 3H), 4.00 (d, CH$_2$), 3.66 (s, OMe); FAB(NBA)-MS: [M+H]=415.0697 (Calcd for C$_{16}$H$_{16}$N$_4$O$_6$SNa=415.0688).

Part B: Synthesis of [$^{99m}$Tc(HYNIC-Gly-OMe)(tricine) (TPPTS)]

To a 10 mL vial was added 0.4 mL of tricine solution (40 mg) in H$_2$O, followed by 0.2 mL of N-(carbomethoxymethyl)-6-(2-sulfobenzaldehyde-hydrazono)nicotinamide sodium salt solution (20 µg), 0.4 mL of $^{99m}$TcO$_4$- solution (50 mCi),and 10 µl of SnCl$_2$.2H$_2$O solution (100 µg) in 0.1N HCl. The reaction mixture was heated at 80° C. for 15 min. To the reaction mixture above was added 0.2 mL of TPPTS solution (2 mg) in H$_2$O . The reaction mixture was heated for another 15 min at 80° C., and was then analyzed by radio-HPLC (method 1). The radiolabeling yield was 91%. R$_t$=7.0 and 7.3 min.

Example 10

Synthesis of [$^{99m}$Tc(DPH) (tricine) (TPPTS)]

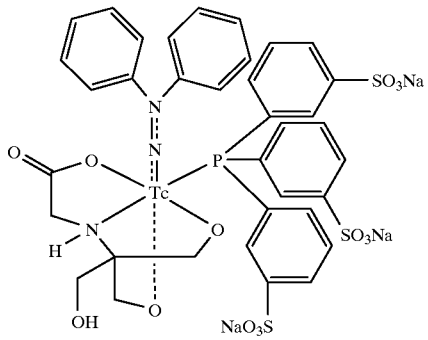

To a 10 mL vial was added 0.4 mL of tricine solution (40 mg) in 25 mM adipic acid buffer (pH 5), followed by 0.1 mL of N,N-diphenylhydrazine mono-hydrochloride solution (100 µg) in 25 mM adipic acid buffer (pH 5), 0.4 mL of $^{99m}$TcO$_4$- solution (40 mCi), 0.2 mL of TPPTS solution (5 mg) in 25 mM adipic acid buffer (pH 5) and 25 µl of SnCl$_2$.2H$_2$O solution (25 µg) in 0.1N HCl. The reaction mixture was heated at 100° C. for 15 min, and was then analyzed by radio-HPLC (method 1). The radiolabeling yield was 92%. R$_t$=10.1 min.

Example 11

Synthesis of [$^{99m}$Tc (DPH) (tricine) (TFP)]

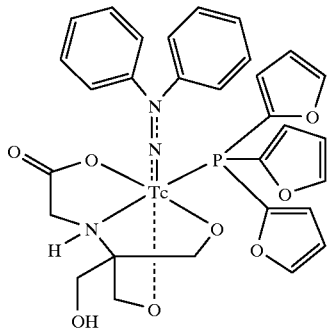

To a 10 mL vial was added 0.4 mL of tricine solution (40 mg) in H$_2$O , followed by 0.1 mL of N,N-diphenylhydrazine mono-hydrochloride solution (25 µg) in H$_2$O, 0.5 mL of $^{99m}$TcO$_4$- solution (50 mCi), 0.2 mL of TFP solution (2 mg) in EtOH and 25 µl of SnCl$_2$.2H$_2$O solution (50 µg in 0.1N HCl). The reaction mixture was heated at 100° C. for 15 min, and was then analyzed by radio-HPLC (method 1). The radiolabeling yield was 97%. R$_t$=18.6 min.

Example 12

Synthesis of [$^{99m}$Tc(DPH) (tricine) (TPPMS)]

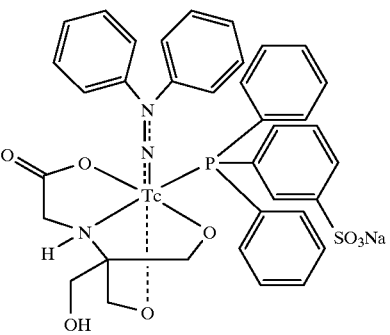

To a 10 mL vial was added 0.4 mL of tricine solution (40 mg) in 25 mM adipic acid buffer (pH 5), followed by 0.1 mL of N,N-diphenylhydrazine mono-hydrochloride solution (100 µg) in 25 mM adipic acid buffer (pH 5), 0.5 mL of $^{99m}$TCO$_4$- solution (50 mCi), 0.2 mL of TPPTS solution (2 mg) in 25 mM adipic acid buffer (pH 5) and 25 µl of SnCl$_2$.2H$_2$O solution (25 µg) in 0.1N HCl. The reaction mixture was heated at 100° C. for 15 min, and was then analyzed by radio-HPLC (method 1). The radiolabeling yield was 95%. R$_t$=18.7 min.

Example 13

Synthesis of [$^{99m}$Tc(DPH) (tricine) (PPh$_3$)]

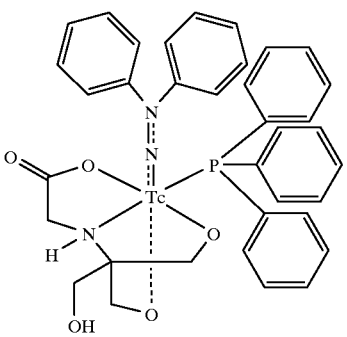

To a clean 10 mL vial was added 0.4 mL of tricine solution (40 mg) in H$_2$O, followed by 0.2 mL of N,N-diphenyihydrazine mono-hydrochloride solution (100 µg) in 50% EtOH, 0.1 mL of $^{99m}$TcO$_4$- solution (50 mCi) in saline, 1.0 mL of triphenylphosphine (PPh$_3$) solution (2 mg) in ethanol, and 25 µl of SnCl$_2$.2H$_2$O solution (25 µg) in 0.1N HCl. The reaction mixture was heated at 100° C. for 30 min, and was then analyzed by radio-HPLC (method 4). The yield was 70%. R$_t$=31.3min.

Example 14

Synthesis of [$^{99m}$Tc (11- (6-hydrazinonicotinamido)undecanoic acid)(tricine)(TPPTS)]

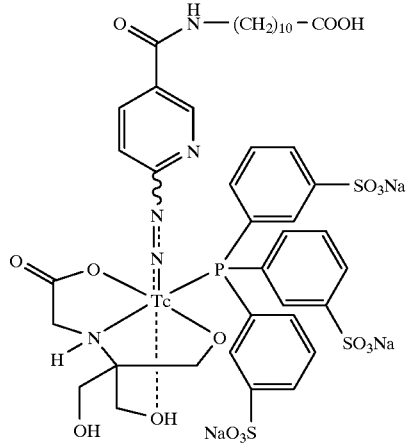

Part A: Synthesis of N-(10-Carboxydecanyl)-6-(2-sulfobenzaldehydehydrazono)nicotinamide Sodium Salt To a solution of 1.4 g (6.95 mmol) of 11-aminoundecanoic acid and 1.0 g (2.27 mmol) of succinimidyl 6-(2-sulfobenzaldehydehydrazono)nicotinate sodium salt in DMF (50 ml) was added Et$_3$N (2.0 ml), and the reaction mixture was allowed to stir at RT for 3 days. The reaction mixture was filtered through celite, concentrated, and triturated with hot EtOAc, to give 1.04 g of a pale yellow powder. Spectral data indicated only partial conversion to the title compound.

To a solution of 0.5 g (2.48 mmol) of 11-aminoundecanoic acid and 0.5 g of the partially converted material in DMF (25 ml) was added Et$_3$N (1.0 ml), and the reaction mixture was allowed to stir at RT for 9 days. The reaction mixture was filtered through celite, concentrated, and triturated with hot EtOAc. The residue was triturated a second time with hot MeOH/EtOAc (1:2 ratio), cooled to RT, and collected by vacuum filtration to provide the title compound (241 mg, 42%) as a pale yellow powder; $^1$H NMR (D$_6$-DMSO) 12.00 (very br s, OH), 11.36 (br s, NH), 9.01 (S, 1H), 8.60 (d, 1H), 8.33 (br t, NH), 8.03 (m, 2H), 7.78 (dd, 1H), 7.30 (m, 3H), 3.23 (br q, CH$_2$), 2.18 (t, CH$_2$), 1.50 (m, 4H), 1.25 (m, 12H); FAB(NBA)-MS: [M+H]=527.1943 (Calcd for C$_{24}$H$_{32}$N$_4$O$_6$SNa=527.1940).

Part B: Synthesis of [$^{99m}$Tc(11-(6-hydrazinonicotinamido)undecanoic acid)(tricine)(TPPTS)]

To a 10 mL vial was added 0.2 mL tricine solution (20 mg) in H$_2$O, 0.4 mL N-(10-carboxydecanyl)-6-(2-sulfobenzaldehydehydrazono)nicotinamide sodium salt solution (40 μg) in EtOH, 0.3 mL $^{99m}$TcO4- (50 mCi) in saline, and 0.5 mL of TPPTS solution (10 mg) in H$_2$O. The reaction mixture was heated at 80° C. for 45 min and was then analyzed by radio-HPLC (method 1). The yield was 85%. R$_t$=9.5 min.

Example 15

Synthesis of [$^{99m}$Tc(11-(6-hydrazinonicotinamido)undecanoic acid) (tricine)(imidazole)]

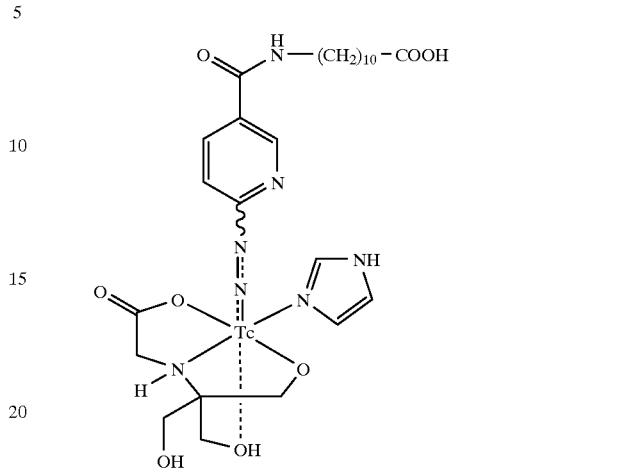

To a 10 mL vial was added 0.4 mL tricine solution (40 mg) in H$_2$O, 0.2 mL N-(10-carboxydecanyl)-6-(2-sulfobenzaldehydehydrazono)nicotinamide sodium salt (10 μg) in EtOH, 0.5 mL $^{99m}$TcO$_4$- (100 mCi) in saline, 0.2 mL of imidazole solution (2 mg) in H$_2$O, and 25 μl of SnCl$_2$.2H$_2$O solution (25 μg) in 0.1N HCl. The reaction mixture was heated at 100° C. for 15 min and was then analyzed by radio-HPLC (method 2). The yield was 95%. R$_t$=15.2 min.

Example 16

Synthesis of [$^{99m}$Tc(11-(6-hydrazinonicotinamido)undecanoic acid) (tricine)(pyridine)]

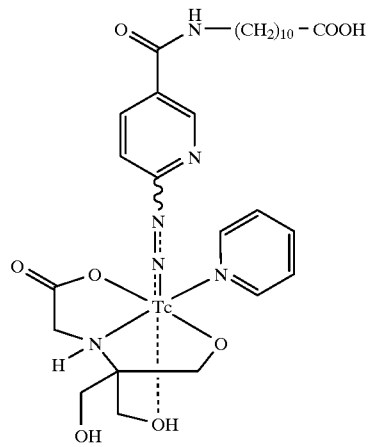

To a 10 mL vial was added 0.4 mL tricine solution (40 mg) in H$_2$O, 0.2 mL N-(10-carboxydecanyl)-6-(2-sulfobenzaldehydehydrazono)nicotinamide sodium salt solution (10 μg) in EtOH, 0.5 mL $^{99m}$TcO$_4$- (100 mCi) in saline, 0.2 mL of pyridine hydrochloride solution (2 mg) in H$_2$O, and 25 μl of SnCl$_2$.2H$_2$O solution (25 μg) in 0.1N HCl. The reaction mixture was heated at 100° C. for 15 min and was then analyzed by radio-HPLC (method 2). The yield was 95%. R$_t$=16.5 min.

Example 17

Synthesis of [$^{99m}$Tc(11-(6-hydrazinonicotinamido)undecanoic acid) (tricine) (TFP)]

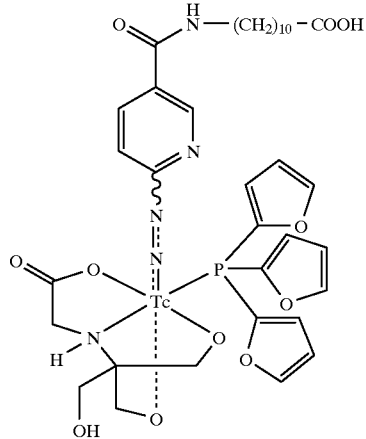

To a 10 mL vial was added 0.4 mL tricine solution (40 mg) in H$_2$O, 0.2 mL N-(10-carboxydecanyl)-6-(2-sulfobenzaldehydehydrazono)nicotinamide sodium salt solution (10 μg) in EtOH, 0.3 ML $^{99m}$TcO$_4$- (~50 mCi) in saline, 0.5 mL of TFP solution (2 mg) in EtOH, and 25 μl of SnCl$_2$.2H$_2$O solution (25 μg) in 0.1N HCl. The reaction mixture was heated at 100° C. for 15 min and then analyzed by radio-HPLC (method 2). The yield was 55%. R$_t$=20.3 min.

Example 18

Synthesis of [$^{99}$Tc(PHY) (tricine) (TPPTS)]

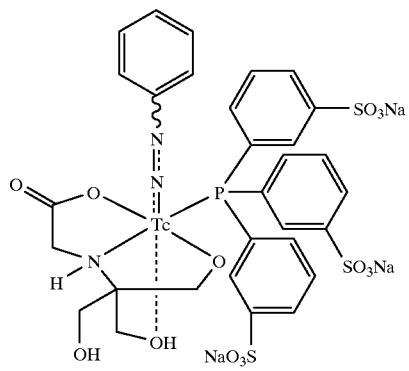

To a 10 mL vial was added 0.4 mL of tricine solution (40 mg) in H$_2$O, followed by 25 μL of phenylhydrazine hydrochloride solution (25 μg) in H$_2$O, 0.3 mL of $^{99m}$TcO$_4$- solution (30 mCi), 0.2 mL of TPPTS solution (2 mg) in H$_2$O and 25 μl of SnCl$_2$.2H$_2$O solution (50 μg) in 0.1N HCl. The reaction mixture was heated at 75° C. for 30 min, and was then analyzed by radio-HPLC (method 1). The radiolabeling yield was 79%. R$_t$=8.2 min.

Example 19

Synthesis of [$^{99m}$Tc(HYLA) (tricine) (TPPTS)]

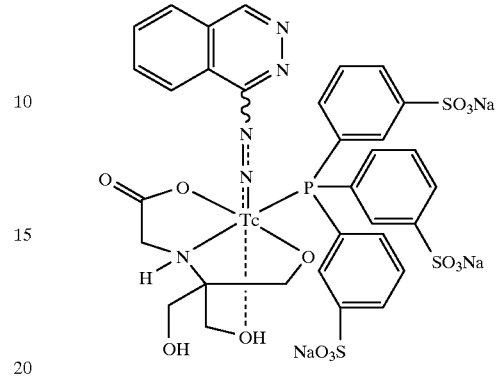

To a 10 mL vial was added 0.4 mL of tricine solution (40 mg) in H$_2$O, followed by 25 μL of hydralazine hydrochloride solution (25 μg) in EtOH, 0.2 mL of $^{99m}$TcO$_4$- solution (50 mCi), 0.2 mL of TPPTS solution (2 mg) in H$_2$O and 25 μl of SnCl$_2$.2H$_2$O solution (25 μg) in 0.1N HCl. The reaction mixture was heated at 100° C. for 10 min, and was then analyzed by radio-HPLC (method 3). The radiolabeling yield was 95%. R$_t$=7.2 min.

Example 20

Synthesis of [$^{99m}$Tc(4-Cl-PHY) (tricine) (TPPTS)]

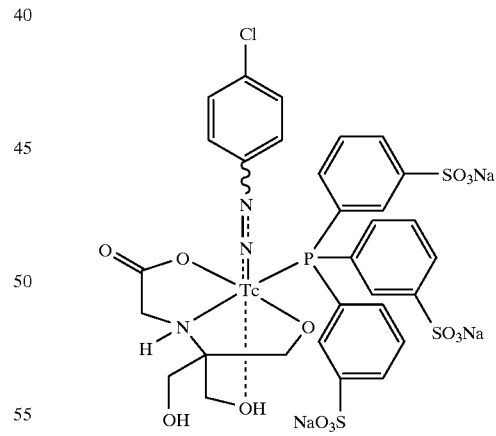

To a 10 mL vial was added 0.4 mL of tricine solution (40 mg) in H$_2$O, followed by 25 μL of 4-chlorophenylhydrazine hydrochloride solution (25 μg) in H$_2$O, 0.2 mL of $^{99m}$TcO$_4$- solution (50 mCi), 0.2 mL of TPPTS solution (2 mg) in H$_2$O and 25 μl of SnCl$_2$.2H$_2$O solution (25 μg) in 0.1N HCl. The reaction mixture was heated at 100° C. for 10 min, and was then analyzed by radio-HPLC (method 3). The radiolabeling yield was 72%. R$_t$8.7 min.

Example 21

Synthesis of [$^{99m}$Tc(HYPY) (hbtris) (TPPTS)]

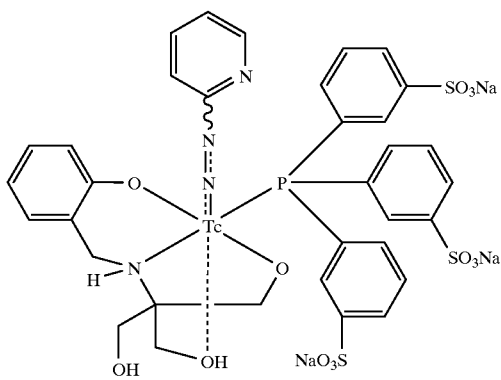

Part A: Synthesis of 2-hydroxyphenylimino-2-hydroxymethyl-1,3-propanediol

To a solution of tris (2.4 g) in hot methanol (30 mL) was added slowly salicylaldehyde (2.5 g) in the same solvent (10 mL). The resulting mixture was refluxed for 30 min, and was then cooled to room temperature. Upon addition of diethyl ether (50 mL), the reaction mixture was kept standing at room temperature for 2–3 hours, during which time bright yellow microcrystals were formed. The bright yellow solid was collected by filtration, washed with diethyl ether, and dried in vacuum. The yield was 4.0 g. The product was used for further reaction without further purification.

Part B: Synthesis of hbtris 2-hydroxyphenylimino-2-hydroxymethyl-1,3-propanediol (5.0 g) was suspended in 30 mL of methanol. Potassium borohydride (KBH$_4$) was added until the yellow color totally disappeared. The reaction mixture was refluxed for an additional 10 min. The solvent was removed under reduced pressure. To the residue was added 2 g of ammonium chloride in 15 mL of water to give a milky solution, which became clear upon heating. The mixture was condensed on a rotary evaporator until white precipitate formed. The residue was cooled in a ice-bath, and the aqueous solution was discarded. To the residue was added 30 mL of absolute ethanol while white solid formed. The white solid was collected by filtration, washed with ethanol (5 mL) and diethyl ether, and dried in air. The yield was 2.6 g. The product was purified by recrystallization from a mixture of water and methanol. Mass spectrum (EI): M/e=228 for [CH$_{11}$H$_{18}$NO$_4$] (M+1)).

Part C: Synthesis of [$^{99m}$Tc(HYPY) (hbtris) (TPPTS)]

To a 10 mL vial was added 0.3 mL of hbtris solution (6 mg) in 25 mM succinate buffer (pH 5), followed by 0.3 mL of 2-hydrazinopyridine hydrochloride solution (30 µg) in 25 mM succinate buffer (pH 5), 0.15 mL of $^{99m}$TcO$_4^-$ solution (70 mCi), 0.3 mL of TPPTS solution (6 mg) in 25 mM adipic acid buffer (pH 5) and 20 µl of SnCl$_2$.2H$_2$O solution (20 µg in 0.1N HCl). The reaction mixture was heated at 100° C. for 10 min, and was then analyzed by radio-HPLC (method 3). The radiolabeling yield was 75%. R$_f$=13.0 min.

Example 22

Synthesis of [$^{99m}$Tc(HYLA) (hbtris) (TPPTS)]

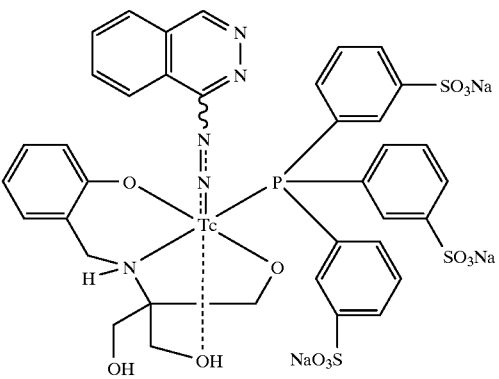

To a 10 mL vial was added 0.5 mL of hbtris solution (5 mg) in 25 mM succinate buffer (pH 5), followed by 0.3 mL of hydralazine hydrochloride solution (30 µg) in 25 mM succinate buffer (pH 5), 0.15 mL of $^{99m}$TcO$_4^-$ solution (70 mCi), 0.3 mL of TPPTS solution (6 mg) in 25 mM adipic acid buffer (pH 5) and 25 µl of SnCl$_2$.2H$_2$O solution (20 µg) in 0.1N HCl. The reaction mixture was heated at 100° C. for 10 min, and was then analyzed by radio-HPLC (method 3). The radiolabeling yield was 63%. R$_f$=9.5 min.

Example 23

Synthesis of [$^{99m}$Tc (4-Cl-PHY) (hbtris) (TPPTS)]

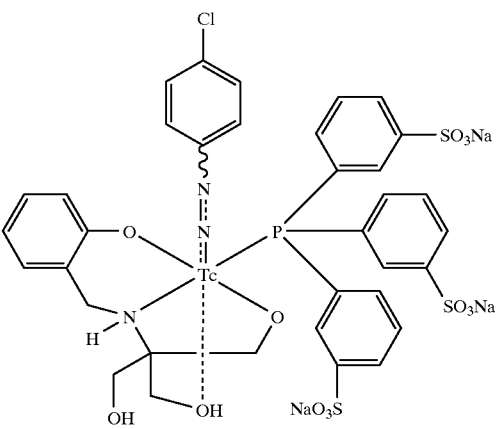

To a 10 mL vial was added 0.5 mL of hbtris solution (5 mg) in 25 mM succinate buffer (pH 5), followed by 0.3 mL of 4-chlorophenylhydrazine hydrochloride solution (30 µg) in 25 mM succinate buffer (pH 5), 0.15 mL of $^{99m}$TcO$_4^-$ solution (70 mCi), 0.3 mL of TPPTS solution (6 mg) in 25 mM adipic acid buffer (pH 5) and 25 µl of SnCl$_2$.2H$_2$O solution (20 µg) in 0.1N HCl. The reaction mixture was heated at 100° C. for 10 min, and was then analyzed by radio-HPLC (method 3). The radiolabeling yield was 32%. R$_f$=12.3 min.

Example 24

Synthesis of [$^{99m}$Tc(4-NO$_2$-PHY) (hbtris) (TPPTS)]

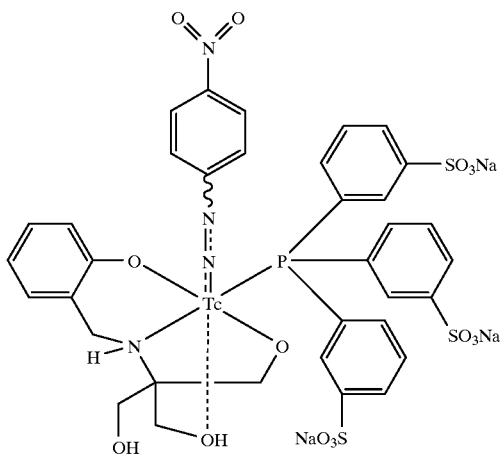

To a 10 mL vial was added 0.5 mL of hbtris solution (5 mg) in 25 mM succinate buffer (pH 5), followed by 0.3 mL of 4-nitrophenylhydrazine solution (30 μg) in 50% EtOH/25 mM succinate buffer (pH 5), 0.15 mL of $^{99m}$TcO$_4^-$ solution (70 mCi), 0.3 mL of TPPTS solution (6 mg) in 25 mM adipic acid buffer (pH 5) and 25 μl of SnCl$_2$.2H$_2$O solution (20 μg) in 0.1N HCl. The reaction mixture was heated at 100° C. for 10 min, and was then analyzed by radio-HPLC (method 3). The radiolabeling yield was 36%. R$_t$=11.7 min.

Example 25

Synthesis of [$^{99}$Tc(HYPY) (tricine) (PPh$_3$)]

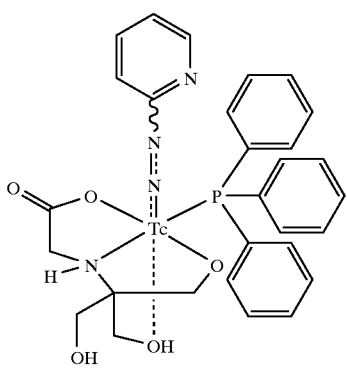

To a solution of [n-Bu$_4$N][TcOCl$_4$] (190 mg, 0.4 mmol) in chloroform (10 mL) was added triphenyiphosphine (265 mg, 10 mmol) in chloroform (10 mL), hydrazinopyridine hydrochloride (91 mg, 8.3 mmol) in a mixture of water (10 mL) and methanol (15 mL), and tricine (350 mg, 2.0 mmol). The solution became dark red immediately after addition of HYPY. The pH in solution was adjusted to 5–6 using tetrabutylammonium hydroxide solution. The solution was transferred to a 150 mL beaker, and the solvents were allowed to evaporate slowly to give a brownish red solid, which was collected by filtration, washed with small amount of acetone, and dried in the air. The yield was 25 mg. Anal. calcd (found) for C$_{29}$H$_{30}$N$_4$O$_5$PTc.1 1.5H$_2$O: C, 51.84 (51.94); H, 4.95 (4.52); N, 8.35 (8.22).

Example 26

Synthesis of [$^{99}$Tc(DPH)(tricine) (PPh$_3$)]

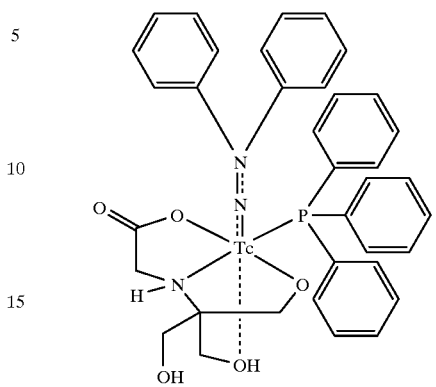

Tricine (570 mg) was dissolved in H$_2$O (7 mL), and triphenyiphosphine (350 mg) and N,N-diphenylhydrazine hydrochloride (200 mg) were dissolved in 25 mL of ethanol. After mixing the two solutions, Bu$_4$N[TcOCl$_4$] ((198 mg) in ethanol (20 mL) was added. The reaction solution was refluxed for 3 hr, and was then cooled to room temperature. Solvents were removed under reduced pressure, and the residue was extracted with chloroform (2×75 mL). The chloroform solution was washed with water (2×30 mL), and was then concentrated to about 10 mL. To the residue was added diethyl ether to give a brown precipitate. The solid was collected by filtration, and washed with diethyl ether. The yield was 54 mg. The sample was analyzed by HPLC using UV detector (λ=340 nm). Co-injection of its $^{99m}$Tc-analog, [$^{99m}$Tc(DPH)(tricine)(PPh$_3$)], the radiopharmaceutical of Example 13, clearly demonstrated that the same complex was made at both the tracer ($^{99m}$Tc) and carrier-added ($^{99}$Tc) levels.

Analytical Methods

The HPLC method 1 used a reverse phase C$_{18}$ Zorbax column (4.6 mm×25 cm, 80 Å pore size) at a flow rate of 1.0 mL/min with a gradient mobile phase from 100% A (10 mM pH 6.0 phosphate buffer) to 75% B (acetonitrile) at 20 min.

The HPLC method 2 used a reverse phase C$_{18}$ Vydac column (4.6 mm×25 cm, 300 Å pore size) at a flow rate of 1.0 mL/min with a gradient mobile phase from 100% A (10 mM pH 6.0 phosphate buffer) to 30% B (acetonitrile) at 15 min and to 75% B (acetonitrile) at 25 min.

The HPLC method 3 used a reverse phase C$_{18}$ Zorbax column (4.6 mm×25 cm, 80 Å pore size) at a flow rate of 1.0 mL/min with a gradient mobile phase from 100% A (10 mM pH 6.0 phosphate buffer) to 30% B (acetonitrile) at 20 min.

The HPLC method 4 used a reverse phase C$_{18}$ Zorbax column (4.6 mm×25 cm, 80 Å pore size) at a flow rate of 1.0 mL/min with a gradient mobile phase from 95% A (10 mM pH 6.0 phosphate buffer) and 5% B (acetonitrile) to 75% B at 45 min.

Utility

The radiopharmaceuticals of the present invention are useful as imaging agents for the heart, brain, lungs, liver and kidneys. A canine imaging and biodistribution model was used to evaluate the radiopharmaceuticals of Examples 5 and 7.

Canine Imaging Model

Adult beagle dogs of either sex (9–13 kg) were anesthetized with pentobarbital sodium (35 mg/kg,i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. All parameters were monitored continuously on a polygraph recorder (model 7D Grass) at a paper speed of 10 mm/min or 25 mm/sec. The right femoral vein was cannulated (PE-240) for drug administration. A control blood sample was collected for hematology analysis on an MCA210 (APTT, PT), K1000 (cell number), and Chrono Log Aggregometer (collagen induced platelet aggregation). Blood samples were also collected immediately after infusion, 30, 60, and 120 minutes post infusion. Samples of blood were retained for blood clearance determination at control, immediately following infusion, 15, 30, 60, 90, and 120 minutes post infusion. Administration of test article was given no earlier than 20 minutes post surgery. The test article was administered as a 10 cc slow infusion over 5 minutes. Images were acquired by a gamma camera over 5 minutes and taken during infusion, 5, 15, 30, 60, 90, 120 minutes post infusion (Digital Dyna Camera, Picker International, Cleveland, Ohio). At the end of the protocol the animal was euthanized with an overdose of pentobarbital and a biodistribution performed. The samples collected for biodistribution (muscle, liver, kidney, bile, spleen, heart, lung thyroid, and urine) and the blood clearance samples were weighed and the amount of activity determined via a gamma well counter (LKB 1282, Wallac Inc).

The radiopharmaceutical of Example 7 was evaluated in the canine imaging model. The rapid clearance from the blood of the radiopharmaceutical is readily apparent as is the predominantly renal excretion. At 120 min post-injection, the vast majority of the radiopharmaceutical is located in the bladder and very little remaining in the blood, the muscle or other organs. This pattern of distribution and excretion is very favorable for renal function studies.

The radiopharmaceutical of Example 5 was also evaluated in the canine imaging model. Rapid blood clearance is again readily apparent but the excretion is predominantly hepatobiliary, a pattern very favorable for imaging the hepatobiliary system. The radiopharmaceutical of Example 5 differs from that of Example 7 in that the sulfonate substituents on the phosphine ligand, $L^3$, and the carboxamide substituent on the ligand, $L^1$, are absent. The absence of the sulfonate substituents renders the radiopharmaceutical neutral in charge and the absence of both the sulfonate groups and the carboxamide group renders it more lipophilic than the anionic radiopharmaceutical of Example 7. These differences account for the dramatically different biological properties of the two complexes, and thus demonstrates the superior ability to control the biological properties of the radiopharmaceuticals of the present invention.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A radiopharmaceutical having the formula:

$$ML^1L^2L^3$$

or a pharmaceutically acceptable salt thereof, wherein,

M is $^{99m}$Tc, $^{186}$Re or $^{188}$Re;

$L^1$ is a ligand having the formula =N—NR$^1$R$^2$ or =N$^+$=NR$^1$;

$R^1$ is selected from the group: aryl substituted with 0–3 $R^3$, 5–10 membered heterocycle containing from 1–4 heteroatoms selected from N, O, and S and substituted with 0–3 $R^3$, $C_1$–$C_{10}$ alkyl substituted with 0–3 $R^3$, and $C_{3-13}$ cycloalkyl substituted with 0–3 $R^3$;

$R^2$ is selected from the group: hydrogen, aryl substituted with 0–3 $R^3$, 5–10 membered heterocycle containing from 1–4 heteroatoms selected from N, O, and S and substituted with 0–3 $R^3$, $C_1$–$C_{10}$ alkyl substituted with 0–3 $R^3$, and $C_{3-13}$ cycloalkyl substituted with 0–3 $R^3$;

$R^3$ is independently selected at each occurrence from the group: =O, F, Cl, Br, I, —CF$_3$, —CN, —CO$_2$R$^4$, —C(=O)R$^4$, —C(=O)N(R$^4$)$_2$, —CH$_2$OR$^4$, —OC(=O)R$^4$, —OC(=O)OR$^4$, —OR$^4$, —OC(=O)N(R$^4$)$_2$, —NR$^4$C(=O)R$^4$, —NR$^4$C(=O)OR$^4$, —NR$^4$C(=O)N(R$^4$)$_2$, —NR$^4$SO$_2$N(R$^4$)$_2$, —NR$^4$SO$_2$R$^4$, —SO$_3$H, —SO$_2$R$^4$, —S(=O)R$^4$, —SO$_2$N(R$^4$)$_2$, —N(R$^4$)$_2$, —N(R$^4$)$_3^+$, —NHC(=NH)NHR$^4$, —C(=NH)NHR$^4$, =NOR$^4$, —NO$_2$, —C(=O)NHOR$^4$, —C(=O)NHN(R$^4$)$_2$, —OCH$_2$CO$_2$H, 2-(1-morpholino)ethoxy, $C_1$–$C_{10}$ alkyl substituted with 0–3 $R^5$, $C_2$–$C_{10}$ alkenyl substituted with 0–3 $R^5$, $C_3$–$C_6$ cycloalkyl substituted with 0–3 $R^5$, aryl substituted with 0–3 $R^5$, and 5–10 membered heterocycle containing from 1–4 heteroatoms selected from N, O, and S and substituted with 0–3 $R^5$;

$R^4$ is independently selected at each occurrence from the group: H, $C_1$–$C_{10}$ alkyl substituted with 0–3 $R^5$, $C_2$–$C_{10}$ alkenyl substituted with 0–3 $R^5$, $C_3$–$C_6$ cycloalkyl substituted with 0–3 $R^5$, aryl substituted with 0–3 $R^5$, and 5–10 membered heterocycle containing from 1–4 heteroatoms selected from N, O, and S and substituted with 0–3 $R^5$;

$R^5$ is independently selected at each occurrence from the group: =O, F, Cl, Br, I, —CF$_3$, —CN, —CO$_2$R$^6$, —C(=O)R$^6$, —C(=O)N(R$^6$)$_2$, —CH$_2$OR$^6$, —OC(=O)R$^6$, —OC(=O)OR$^6$, —OR$^6$, —OC(=O)N(R$^6$)$_2$, —NR$^6$C(=O)R$^6$, —NR$^6$C(=O)OR$^6$, —NR$^6$C(=O)N(R$^6$)$_2$, —NR$^6$SO$_2$N(R$^6$)$_2$, —NR$^6$SO$_2$R$^6$, —SO$_3$H, —SO$_2$R$^6$, —S(=O)R$^6$, —SO$_2$N(R$^6$)$_2$, —N(R$^6$)$_2$, —N(R$^6$)$_3^+$, —NHC(=NH)NHR$^6$, —C(=NH)NHR$^6$, =NOR$^6$, —NO$_2$, —C(=O)NHOR$^6$, —C(=O)NHNR$^6$R$^6$, —OCH$_2$CO$_2$H, and phenyl;

provided that when $R^1$ is pyridyl-$R^3$, $R^3$ is C(O)N(R$^4$)$_2$, and one $R_4$ is alkyl-(R$^5$)$_2$, then $R^5$ at each occurrence is other than phenyl;

$R^6$ is independently selected at each occurrence from the group: H, and $C_1$–$C_6$ alkyl;

$L^2$ is a ligand having the formula $$(R^{11})(R^{12})(R^{13})C-N(R^7)-(C(R^8)(R^9))_m-R^{10}$$

$R^7$ is selected from the group: hydrogen, hydroxy, aryl substituted with 0–3 $R^{14}$, and $C_1$–$C_{10}$ alkyl substituted with 0–3 $R^{15}$;

alternatively, $R^7$ and $R^8$ together form a 3–6 membered heterocycle containing from 1–4 heteroatoms selected from N, O, and S and substituted with 0–3 $R^{14}$;

$R^8$ and $R^9$ are independently selected from the group: hydrogen, hydroxyl, 5–10 membered heterocycle containing from 1–4 heteroatoms selected from N, O, and S and substituted with 0–3 $R^{14}$, $C_1$–$C_{10}$ alkyl substituted with 0–3 $R^{15}$, and $C_{3-13}$ cycloalkyl substituted with 0–3 $R^{15}$;

alternatively, $R^8$ and $R^9$ can be taken together to form a $C_3$–$C_6$ cycloalkyl substituted with 0–3 $R^{15}$;

$R^{10}$ is selected from the group: —COOH, phenyl substituted with 0–3 $R^{14}$, and 5–10 membered heterocycle containing from 1–4 heteroatoms selected from N, O, and S and substituted with 0–3 $R^{14}$;

$R^{11}$ and $R^{12}$ are independently selected at each occurrence from the group: H, —OH, —COOH, 5–10 membered heterocycle containing from 1–4 heteroatoms selected from N, O, and S and substituted with 0–3 $R^{14}$, $C_1$–$C_{10}$ alkyl substituted with 0–3 $R^{15}$, and $C_{3-13}$ cycloalkyl substituted with 0–3 $R^{15}$;

alternatively, $R^7$ and $R^{11}$ together form a 3–6 membered heterocycle containing from 1–4 heteroatoms selected from N, O, and S and substituted with 0–3 $R^{14}$;

$R^{13}$ is —$CH_2OH$, or —$CH_2CH_2OH$;

m is 0–2;

$R^{14}$ is independently selected at each occurrence from the group: $C_1$–$C_5$ alkyl substituted with 0–3 $R^{15}$, $C_2$–$C_5$ alkenyl substituted with 0–3 $R^{15}$, $C_3$–$C_6$ cycloalkyl substituted with 0–3 $R^{15}$, aryl substituted with 0–3 $R^{15}$, and 5–10 membered heterocycle containing from 1–4 heteroatoms selected from N, O, and S and substituted with 0–3 $R^{15}$, F, Cl, Br, I, —$CF_3$, —CN, —$CO_2R^{16}$, —C(=O)$R^{16}$, —C(=O)N($R^{16}$)$_2$, —$CH_2OR^{16}$, —OC(=O)$R^{16}$, —OC(=O)O$R^{16}$, —O$R^{16}$, —OC(=O)N($R^{16}$)$_2$, —N$R^{16}$C(=O)$R^{16}$, —N$R^{16}$C(=O)O$R^{16}$, —N$R^{16}$C(=O)N($R^{16}$)$_2$, —N$R^{16}$SO$_2$N($R^{16}$)$_2$, —N$R^{16}$SO$_2R^{16}$—SO$_3$H, —SO$_2R^{16}$, —SO$_2$N($R^{16}$)$_2$—PO$_3$H$_2$, —NHC(=NH)NH$R^{16}$, —C(=NH)NH$R^{16}$, NO$_2$, —OCH$_2$CO$_2$H;

$R^{15}$ is independently selected at each occurrence from the group: =O, F, Cl, Br, I, —$CF_3$, —CN, —$CO_2R^{16}$, —C(=O)$R^{16}$, —C(=O)N($R^{16}$)$_2$, —$CH_2OR^{16}$, —OC(=O)$R^{16}$, —OC(=O)O$R^{16}$, —O$R^{16}$, —OC(=O)N($R^{16}$)$_2$, —N$R^{16}$C(=O)$R^{16}$, —N$R^{16}$C(=O)O$R^{16}$, —N$R^{16}$C(=O)N($R^{16}$)$_2$, —N$R^{16}$SO$_2$N($R^{16}$)$_2$, —N$R^{16}$SO$_2R^{16}$—SO$_3$H, —SO$_2R^{16}$, —SO$_2$N($R^{16}$)$_2$, —PO$_3$H$_2$, —NHC(=NH)NH$R^{16}$, —C(=NH)NH$R^{16}$, NO$_2$, and —OCH$_2$CO$_2$H;

$R^{16}$ is independently selected at each occurrence from the group: hydrogen, and $C_1$–$C_6$ alkyl;

$L^3$ is a ligand having a formula selected from the group:

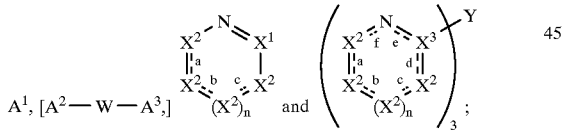

$A^1$ is selected from the group: $PR^{17}R^{18}R^{19}$ and $AsR^{17}R^{18}R^{19}$;

$R^{17}$, $R^{18}$, and $R^{19}$ are independently selected at each occurrence from the group: aryl substituted with 0–3 $R^{20}$, 5–10 membered heterocycle containing from 1–4 heteroatoms selected from N, O, and S and substituted with 0–3 $R^{20}$, aralkyl substituted with 0–3 $R^{20}$, arylalkaryl substituted with 0–3 $R^{20}$, $C_1$–$C_{10}$ alkyl substituted with 0–3 $R^{21}$, and $C_{3-13}$ cycloalkyl substituted with 0–3 $R^{21}$;

$R^{20}$ is independently selected at each occurrence from the group: $C_1$–$C_5$ alkyl substituted with 0–3 $R^{21}$, $C_2$–$C_5$ alkenyl substituted with 0–3 $R^{21}$, $C_3$–$C_6$ cycloalkyl substituted with 0–3 $R^{21}$, aryl substituted with 0–3 $R^{21}$, and 5–10 membered heterocycle containing from 1–4 heteroatoms selected from N, O, and S and substituted with 0–3 $R^{21}$, F, Cl, Br, I, —$CF_3$, —CN, —$CO_2R^{22}$, —C(=O)$R^{22}$, —C(=O)N($R^{22}$)$_2$, —$CH_2OR^{22}$, —OC(=O)$R^{22}$, —OC(=O)O$R^{22}$, —O$R^{22}$, —OC(=O)N($R^{22}$)$_2$, —N$R^{22}$C(=O)$R^{22}$, —N$R^{22}$C(=O)O$R^{22}$, —N($R^{22}$)$_2$, —N($R^{22}$)$_3^+$, —N$R^{22}$C(=O)N($R^{22}$)$_2$, —N$R^{22}$SO$_2$N($R^{22}$)$_2$, —N$R^{22}$SO$_2R^{22}$, —SO$_3$H, —SO$_2R^{22}$, —SO$_2$N($R^{22}$)$_2$, —PO$_3$H$_2$, —NHC(=NH)NH$R^{22}$, —C(=NH)NH$R^{22}$, NO$_2$, and —OCH$_2$CO$_2$H;

$R^{21}$ is independently selected at each occurrence from the group: =O, F, Cl, Br, I, —$CF_3$, —CN, —$CO_2R^{22}$, —C(=O)$R^{22}$, —C(=O)N($R^{22}$)$_2$, —$CH_2OR^{22}$, —OC(=O)$R^{22}$, —OC(=O)O$R^{22}$, —O$R^{22}$, —OC(=O)N($R^{22}$)$_2$, —N$R^{22}$C(=O)$R^{22}$, —N$R^{22}$C(=O)O$R^{22}$, —N$R^{22}$C(=O)N($R^{22}$)$_2$, —N$R^{22}$SO$_2$N($R^{22}$)$_2$, —N$R^{22}$SO$_2R^{22}$, —SO$_3$H, —SO$_2R^{22}$, —S(=O)$R^{22}$, —SO$_2$N($R^{22}$)$_2$, —N($R^{22}$)$_2$, —N($R^{22}$)$_3^+$, —PO$_3$H$_2$, —NHC(=NH)NH$R^{22}$, —C(=NH)NH$R^{22}$, =NO$R^{22}$, NO$_2$, —C(=O)NHO$R^{22}$, —C(=O)NHN($R^{22}$)$_2$, —OCH$_2$CO$_2$H;

$R^{22}$ is independently selected at each occurrence from the group: hydrogen and $C_1$–$C_6$ alkyl;

$X^1$ is independently selected at each occurrence from the group: $CR^{23}$ and N;

$X^2$ is independently selected at each occurrence from the group: $CR^{23}$, $CR^{23}R^{23}$, N, $NR^{23}$, O and S;

$X^3$ is independently selected at each occurrence from the group: C, $CR^{23}$, and N;

provided the total number of heteroatoms, $X^1$, $X^2$, and $X^3$ in each ring of the ligand, $L^3$, is 1, 2, 3, or 4;

Y is selected from the group: $BR^{23-}$, $CR^{23}$, (P=O), (P=S);

n is 0 or 1;

a, b, c, d, e and f indicate the positions of optional double bonds, provided that one of e and f is a double bond;

$R^{23}$ is independently selected at each occurrence from the group: H, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, $C_1$–$C_{10}$ alkoxy substituted with 0–3 $R^{24}$, $C_{3-13}$ carbocycle substituted with 0–3 $R^{24}$, and $R^{24}$;

or, alternatively, two $R^{23}$ may be taken together with the atom or atoms to which they are attached to form a fused aromatic substituted with 0–3 $R^{24}$, $C_{5-7}$ carbocyclic ring substituted with 0–3 $R^{24}$ or 5–7 membered heterocycle containing from 1–4 heteroatoms selected from N, O, and S, and substituted with 0–3 $R^{24}$;

$R^{24}$ is independently selected at each occurrence from the group: =O, F, Cl, Br, I, —$CF_3$, —CN, —NO$_2$, —$CO_2R^{25}$, —C(=O)$R^{25}$, —C(=O)N($R^{25}$)$_2$, —N($R^{25}$)$_3^+$, —$CH_2OR^{25}$, —OC(=O)$R^{25}$, —OC(=O)O$R^{25}$, —O$R^{25}$, —OC(=O)N($R^{25}$)$_2$, —N$R^{25}$C(=O)$R^{25}$, —N$R^{25}$C(=O)O$R^{25}$, —N$R^{25}$C(=O)N($R^{25}$)$_2$, —N$R^{25}$SO$_2$N($R^{25}$)$_2$, —N$R^{25}$SO$_2R^{25}$, —SO$_3$H, —SO$_2R^{25}$, —SO$_2$N($R^{25}$)$_2$, —N($R^{25}$)$_2$, —OCH$_2$CO$_2$H; and $R^{25}$ is independently selected at each occurrence from the group: hydrogen and $C_1$–$C_6$ alkyl.

2. A radiopharmaceutical according to claim 1, wherein:

M is $^{99m}$Tc;

$R^1$ is selected from the group: aryl substituted with 0–3 $R^3$, and 5–10 membered heterocycle containing from 1–4 heteroatoms selected from N, O, and S and substituted with 0–3 $R^3$;

$R^2$ is selected from the group: hydrogen, aryl substituted with 0–3 $R^3$, and 5–10 membered heterocycle containing from 1–4 heteroatoms selected from N, O, and S and substituted with 0–3 $R^3$;

$R^3$ is independently selected at each occurrence from the group: F, Cl, Br, I, $-CO_2R^4$, $-C(=O)N(R^4)_2$, $-CH_2OR^4$, $-OC(=O)R^4$, $-OR^4$, $-NR^4C(=O)R^4$, $-NR^4SO_2R^4$, $-SO_3H$, $-SO_2N(R^4)_2$, $-N(R^4)_2$, $-N(R^4)_3^+$, $-NO_2$, $-OCH_2CO_2H$, and $C_1-C_{10}$ alkyl substituted with 0–3 $R^5$;

$R^4$ is independently selected at each occurrence from the group: H, and $C_1-C_{10}$ alkyl substituted with 0–3 $R^5$;

$R^5$ is independently selected at each occurrence from the group: =O, F, Cl, Br, I, $-CO_2R^6$, $-C(=O)N(R^6)_2$, $-CH_2OR^6$, $-OC(=O)R^6$, $-OR^6$, $-NR^6C(=O)R^6$, $-NR^6SO_2R^6$, $-SO_3H$, $-SO_2N(R^6)_2$, $-N(R^6)_2$, $-N(R^6)_3^+$, $-NO_2$, $-OCH_2CO_2H$, and phenyl;

$R^7$ is selected from the group: hydrogen, and $C_1-C_{10}$ alkyl substituted with 0–3 $R^{15}$;

$R^8$ and $R^9$ are independently selected from the group: hydrogen, hydroxyl, and $C_1-C_{10}$ alkyl substituted with 0–3 $R^{15}$;

$R^{11}$ and $R^{12}$ are independently selected at each occurrence from the group: H, $-OH$, and $C_1-C_{10}$ alkyl substituted with 0–3 $R^{15}$;

m is 0–1;

$R^{14}$ is independently selected at each occurrence from the group: $C_1-C_5$ alkyl substituted with 0–3 $R^{15}$, F, Cl, Br, I, $-CO_2R^{16}$, $-C(=O)N(R^{16})_2$, $-CH_2OR^{16}$, $-OC(=O)R^{16}$, $-OR^{16}$, $-NR^{16}C(=O)R^{16}$, $-NR^{16}SO_2R^{16}$, $-SO_3H$, $-SO_2N(R^{16})_2$, $-PO_3H_2$, $-NO_2$, and $-OCH_2CO_2H$;

$R^{15}$ is independently selected at each occurrence from the group: =O, F, Cl, Br, I, $-CO_2R^{16}$, $-C(=O)N(R^{16})_2$, $-CH_2OR^{16}$, $-OC(=O)R^{16}$, $-OR^{16}$, $-NR^{16}C(=O)R^{16}$, $-NR^{16}SO_2R^{16}$, $-SO_3H$, $-SO_2N(R^{16})_2$, $-PO_3H_2$, and $-OCH_2CO_2H$;

$L^3$ is a ligand having a formula selected from the group:

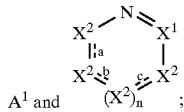

$A^1$ is $PR^{17}R^{18}R^{19}$;

$R^{17}$, $R^{18}$, and $R^{19}$ are independently selected from the group: aryl substituted with 0–3 $R^{20}$, 5–10 membered heterocycle containing from 1–4 heteroatoms selected from N, O, and S and substituted with 0–3 $R^{20}$, and $C_1-C_{10}$ alkyl substituted with 0–3 $R^{21}$;

$R^{20}$ is independently selected at each occurrence from the group: $C_1-C_5$ alkyl substituted with 0–3 $R^{21}$, F, Cl, Br, I, $-CO_2R^{22}$, $-C(=O)N(R^{22})_2$, $-CH_2OR^{22}$, $-OC(=O)R^{22}$, $-OR^{22}$, $-NR^{22}C(=O)R^{22}$, $-NR^{22}SO_2R^{22}$, $-SO_3H$, $-SO_2N(R^{22})_2$, $-N(R^{22})_2$, $-N(R^{22})_3^+$, $-PO_3H_2$, and $-OCH_2CO_2H$;

$R^{21}$ is independently selected at each occurrence from the group: =O, F, Cl, Br, I, $-CO_2R^{22}$, $-C(=O)N(R^{22})_2$, $-CH_2OR^{22}$, $-OC(=O)R^{22}$, $-PO_3H_2$, $-OR^{22}$, $-NR^{22}C(=O)R^{22}$, $-NR^{22}SO_2R^{22}$, $-SO_3H$, $-SO_2N(R^{22})_2$, $-N(R^{22})_2$, $-N(R^{22})_3^+$, and $-OCH_2CO_2H$;

$x^2$ is independently selected at each occurrence from the group: $CR^{23}$, $CR^{23}R^{23}$, N, $NR^{23}$, and O;

provided the total number of heteroatoms, $X^1$ and $X^2$, is 1, 2, 3, or 4;

$R^{23}$ is independently selected at each occurrence from the group: H, $C_1-C_3$ alkyl substituted with 0–3 $R^{24}$, aryl substituted with 0–3 $R^{24}$, and $R^{24}$;

alternatively, two $R^{23}$'s may be taken together with the atom or atoms to which they are attached to form a fused aromatic substituted with 0–3 $R^{24}$ or a 5–7 membered heterocyclic ring containing from 1–4 heteroatoms selected from N, O, and S and substituted with 0–3 $R^{24}$; and, $R^{24}$ is independently selected at each occurrence from the group: $-NO_2$, $-CO_2R^{25}$, $-OR^{25}$, $-SO_3H$, and $-OCH_2CO_2H$.

3. A radiopharmaceutical according to claim 2, wherein:

$R^1$ is selected from the group: aryl substituted with 0–1 $R^3$, and heterocycle substituted with 0–1 $R^3$, wherein said heterocycle is pyridine or phthalazine;

$R^2$ is selected from the group: hydrogen, and aryl substituted with 0–1 $R^3$;

$R^3$ is independently selected at each occurrence from the group: Cl, $-CO_2R^4$, $-C(=O)N(R^4)_2$, $-OR^4$, $-SO_3H$, and $-NO_2$;

$R^4$ is independently selected at each occurrence from the group: H, and $C_1-C_{10}$ alkyl substituted with 0–2 $R^5$;

$R^5$ is selected from the group: $-CO_2R^6$, $-OR^6$, and phenyl;

$R^6$ is independently selected from the group: H and methyl;

$R^7$, $R^8$, and $R^9$ are each hydrogen;

$R^{10}$ is selected from the group: $-COOH$, and 2-hydroxyphenyl;

m is 0–1, provided that when $R^{10}$ is $-COOH$, m is 1;

$R^{11}$, $R^{12}$, and $R^{13}$ are each $-CH_2OH$;

$A^1$ is $PR^{17}R^{18}R^{19}$;

$R^{17}$, $R^{18}$ and $R^{19}$ are independently selected from the group: aryl substituted with 0–1 $R^{20}$, 5–10 membered heterocycle containing from 1–4 heteroatoms selected from N, O, and S and substituted with 0–1 $R^{20}$, and $C_1-C_3$ alkyl substituted with 0–1 $R^{21}$;

$R^{20}$ is independently selected at each occurrence from the group: $-CO_2R^{22}$, $-OR^{22}$, and $-SO_3H$;

$R^{21}$ is selected from the group: $-CO_2R^{22}$, and $-OR^{22}$;

$R^{22}$ is independently selected from the group: H, and methyl;

$X^1$ is CH; and, $x^2$ is independently selected at each occurrence from the group: CH, and NH, provided only one $X^2$ is NH.

4. A radiopharmaceutical according to claim 3, wherein the radiopharmaceutical is selected from the group:

[$^{99m}$Tc(HYPY) (tricine) (TPPTS)];

[$^{99m}$Tc(HYPY) (tricine) (TPPMS)];

[$^{99m}$Tc(HYPY) (tricine)(imidazole)];

[$^{99m}$Tc(HYPY) (tricine) (pyridine)];

[$^{99m}$Tc(HYPY) (tricine) (TFP)]i;

[$^{99m}$Tc(HYPY) (tricine) (PPh$_3$)];

[$^{99m}$Tc(HYNICamide) (tricine) (TPPTS)];

[$^{99m}$Tc(HYNIC-DMA) (tricine) (TPPTS)];

[$^{99m}$Tc(HYNIC-Gly-OMe) (tricine) (TPPTS)];

[$^{99m}$Tc(HYNIC-D-Phe-OMe)(tricine)(TPPTS)];

[$^{99m}$Tc(DPH) (tricine) (TPPTS)];

[$^{99m}$Tc(DPH) (tricine) (TFP)];

[$^{99m}$Tc(DPH) (tricine) (TPPMS)];

[$^{99m}$Tc(DPH) (tricine) (PPh$_3$)];

[$^{99m}$Tc(11-(6-hydrazinonicotinamido)undecanoic acid) (tricine)(TPPTS)];

[$^{99m}$Tc(11-(6-hydrazinonicotinamido)undecanoic acid) (tricine)(imidazole)];

[$^{99m}$Tc(11-(6-hydrazinonicotinamido)undecanoic acid) (tricine)(pyridine)];

[$^{99m}$Tc(11-(6-hydrazinonicotinamido)undecanoic acid) (tricine)(TFP)];

[$^{99m}$Tc(PHY) (tricine) (TPPTS)];

[$^{99m}$Tc(HYLA) (tricine) (TPPTS)];

[$^{99m}$Tc(4-Cl-PHY) (tricine) (TPPTS)];

[$^{99m}$Tc(HYPY) (hbtris) (TPPTS)];

[$^{99m}$Tc(HYLA) (hbtris) (TPPTS)];

[$^{99m}$Tc(4-Cl-PHY) (hbtris) (TPPTS)]; and,

[$^{99m}$Tc(4-NO$_2$-PHY) (hbtris) (TPPTS)].

5. A kit for preparing a radiopharmaceutical, comprising:

(a) a pharmaceutically acceptable first ligand having the formula $R^1R^2N-NH_2$ or a ligand precursor having the formula $R^1R^2N-N=CR^{26}R^{27}$;

(b) a pharmaceutically acceptable second ligand having the formula:

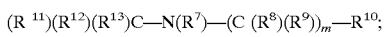

and, (c) a pharmaceutically acceptable third ligand having a formula selected from the group:

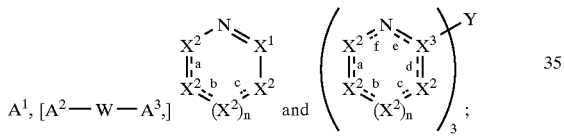

$R^1$ is selected from the group: aryl substituted with 0–3 $R^3$, 5–10 membered heterocycle containing from 1–4 heteroatoms selected from N, O, and S and substituted with 0–3 $R^3$, $C_1$–$C_{10}$ alkyl substituted with 0–3 $R^3$, and cycloalkyl substituted with 0–3 $R^3$;

$R^2$ is selected from the group: hydrogen, aryl substituted with 0–3 $R^3$, 5–10 membered heterocycle containing from 1–4 heteroatoms selected from N, O, and S and substituted with 0–3 $R^3$, $C_1$–$C_{10}$ alkyl substituted with 0–3 $R^3$, and cycloalkyl substituted with 0–3 $R^3$;

$R^3$ is independently selected at each occurrence from the group: =O, F, Cl, Br, I, —CF$_3$, —CN, —CO$_2$R$^4$, —C(=O)R$^4$, —C(=O)N(R$^4$)$_2$, —CH$_2$OR$^4$, —OC(=O)R$^4$, —OC(=O)OR$^4$, —OR$^4$, —OC(=O)N(R$^4$)$_2$, —NR$^4$C(=O)R$^4$, —NR$^4$C(=O)OR$^4$, —NR$^4$C(=O)N(R$^4$)$_2$, —NR$^4$SO$_2$N(R$^4$)$_2$, —NR$^4$SO$_2$R$^4$, —SO$_3$H, —SO$_2$R$^4$, —S(=O)R$^4$, —SO$_2$N(R$^4$)$_2$, —N(R$^4$)$_2$, —N(R$^4$)$_3^+$, —NHC(=NH)NHR$^4$, —C(=NH)NHR$^4$, =NOR$^4$, —NO$_2$, —C(=O)NHOR$^4$, —C(=O)NHN(R$^4$)$_2$, —OCH$_2$C$_2$H, 2-(1-morpholino)ethoxy, $C_1$–$C_{10}$ alkyl substituted with 0–3 $R^5$, $C_2$–$C_{10}$ alkenyl substituted with 0–3 $R^5$, $C_3$–$C_6$ cycloalkyl substituted with 0–3 $R^5$, aryl substituted with 0–3 $R^5$, and 5–10 membered heterocycle containing from 1–4 heteroatoms selected from N, O, and S and substituted with 0–3 $R^5$;

$R^4$ is independently selected at each occurrence from the group: H, $C_1$–$C_{10}$ alkyl substituted with 0–3 $R^5$, $C_2$–$C_{10}$ alkenyl substituted with 0–3 $R^5$, $C_3$–$C_6$ cycloalkyl substituted with 0–3 $R^5$, aryl substituted with 0–3 $R^5$, and 5–10 membered heterocycle containing from 1–4 heteroatoms selected from N, O, and S and substituted with 0–3 $R^5$;

$R^5$ is independently selected at each occurrence from the group: =O, F, Cl, Br, I, —CF$_3$, —CN, —CO$_2$R$^6$, —C(=O)R$^6$, —C(=O)N(R$^6$)$_2$, —CH$_2$OR$^6$, —OC(=O)R$^6$, —OC(=O)OR$^6$, —OR$^6$, —OC(=O)N(R$^6$)$_2$, —NR$^6$C(=O)R$^6$, —NR$^6$C(=O)OR$^6$, —NR$^6$C(=O)N(R$^6$)$_2$, —NR$^6$SO$_2$N(R$^6$)$_2$, —NR$^6$SO$_2$R$^6$, —SO$_3$H, —SO$_2$R$^6$, —S(=O)R$^6$, —SO$_2$N(R$^6$)$_2$, —N(R$^6$)$_2$, —N(R$^6$)$_3^+$, —NHC(=NH)NHR$^6$, —C(=NH)NHR$^6$, =NOR$^6$, —NO$_2$, —C(=O)NHOR$^6$, —C(=O)NHNR$^6$R$^6$, —OCH$_2$CO$_2$H, and phenyl;

provided that when $R^1$ is pyridyl-$R^3$, $R^3$ is C(O)N(R$^4$)$_2$, and one $R_4$ is alkyl-(R$^5$)$_2$, then $R^5$ at each occurrence is other than phenyl;

$R^6$ is independently selected at each occurrence from the group: H, and $C_1$–$C_6$ alkyl;

$R^7$ is selected from the group: hydrogen, hydroxy, aryl substituted with 0–3 $R^{14}$, and $C_{1-C10}$ alkyl substituted with 0–3 $R^{15}$;

alternatively, $R^7$ and $R^8$ together form a 3–6 membered heterocycle containing from 1–4 heteroatoms selected from N, O, and S and substituted with 0–3 $R^{14}$;

$R^8$ and $R^9$ are independently selected from the group: hydrogen, hydroxyl, 5–10 membered heterocycle containing from 1–4 heteroatoms selected from N, O, and S and substituted with 0–3 $R^{14}$, $C_1$–$C_{10}$ alkyl substituted with 0–3 $R^{15}$, and cycloalkyl substituted with 0–3 $R^{15}$;

alternatively, $R^8$ and $R^9$ can be taken together to form a $C_3$–$C_6$ cycloalkyl substituted with 0–3 $R^{15}$;

$R^{10}$ is selected from the group: —COOH, phenyl substituted with 0–3 $R^{14}$, and 5–10 membered heterocycle containing from 1–4 heteroatoms selected from N, O, and S and substituted with 0–3 $R^{14}$;

$R^{11}$ and $R^{12}$ are independently selected at each occurrence from the group: H, —OH, —COOH, 5–10 membered heterocycle containing from 1–4 heteroatoms selected from N, O, and S and substituted with 0–3 $R^{14}$, $C_1$–$C_{10}$ alkyl substituted with 0–3 $R^{15}$, and cycloalkyl substituted with 0–3 $R^{15}$;

alternatively, $R^7$ and $R^{11}$ together form a 3–6 membered heterocycle containing from 1–4 heteroatoms selected from N, O, and S and substituted with 0–3 $R^{14}$;

$R^{13}$ is —CH$_2$OH, or —CH$_2$CH$_2$O H;

m is 0–2;

$R^{14}$ is independently selected at each occurrence from the group: $C_1$–$C_5$ alkyl substituted with 0–3 $R^{15}$, $C_2$–$C_5$ alkenyl substituted with 0–3 $R^{15}$, $C_3$–$C_6$ cycloalkyl substituted with 0–3 $R^{15}$, aryl substituted with 0–3 $R^{15}$, and 5–10 membered heterocycle containing from 1–4 heteroatoms selected from N, O, and S and substituted with 0–3 $R^{15}$, F, Cl, Br, I, —CF$_3$, —CN, —CO$_2$R$^{16}$, —C(=O)R$^{16}$, —C(=O)N(R$^{16}$)$_2$, —CH$_2$OR$^{16}$, —OC(=O)R$^{16}$, —OC(=O)OR$^{16}$, —OR$^{16}$, —OC(=O)N(R$^{16}$)$_2$, —NR$^{16}$C(=O)R$^{16}$, —NR$^{16}$C(=O)OR$^{16}$, —NR$^{16}$C(=O)N(R$^{16}$)$_2$, —NR$^{16}$SO$_2$N(R$^{16}$)$_2$, —NR$^{16}$SO$_2$R$^{16}$, —SO$_3$H, —SO$_2$R$^{16}$, —SO$_2$N(R$^{16}$)$_2$, —PO$_3$H$_2$, —NHC (=NH)NHR$^{16}$, —C(=NH)NHR$^{16}$, NO$_2$, —OCH$_2$CO$_2$H;

R$^{15}$ is independently selected at each occurrence from the group: =O, F, Cl, Br, I, —CF$_3$, —CN, —CO$_2$R$^{16}$, —C(=O)R$^{16}$, —C(=O)N(R$^{16}$)$_2$, —CH$_2$OR$^{16}$, —OC(=O)R$^{16}$, —OC(=O)OR$^{16}$, —OR$^{16}$, —OC(=O)N(R$^{16}$)$_2$, —NR$^{16}$C(=O)R$^{16}$, —NR$^{16}$C(=O)OR$^{16}$, —NR$^{16}$C(=O)N(R$^{16}$)$_2$, —NR$^{16}$SO$_2$N(R$^{16}$)$_2$, —NR$^{16}$SO$_2$R$^{16}$, —SO$_3$H, —SO$_2$R$^{16}$, —SO$_2$N(R$^{16}$)$_2$, —PO$_3$H$_2$, —NHC(=NH)NHR$^{16}$, —C(=NH)NHR$^{16}$, NO$_2$, and —OCH$_2$CO$_2$H;

R$^{16}$ is independently selected at each occurrence from the group: hydrogen, and C$_1$–C$_6$ alkyl;

A$^1$ is selected from the group: PR$^{17}$R$^{18}$R$^{19}$ and AsR$^{17}$R$^{18}$R$^{19}$;

R$^{17}$, R$^{18}$, and R$^{19}$ are independently selected at each occurrence from the group: aryl substituted with 0–3 R$^{20}$, 5–10 membered heterocycle containing from 1–4 heteroatoms selected from N, O, and S and substituted with 0–3 R$^{20}$, aralkyl substituted with 0–3 R$^{20}$, arylalkaryl substituted with 0–3 R$^{20}$, C$_1$–C$_{10}$ alkyl substituted with 0–3 R$^{21}$, and cycloalkyl substituted with 0–3 R$^{21}$;

R$^{20}$ is independently selected at each occurrence from the group: C$_1$–C$_5$ alkyl substituted with 0–3 R$^{21}$, C$_2$–C$_5$ alkenyl substituted with 0–3 R$^{21}$, C$_3$–C$_6$ cycloalkyl substituted with 0–3 R$^{21}$, aryl substituted with 0–3 R$^{21}$, and 5–10 membered heterocycle containing from 1–4 heteroatoms selected from N, O, and S and substituted with 0–3 R$^{21}$, F, Cl, Br, I, —CF$_3$, —CN, —CO$_2$R$^{22}$, —C(=O)R$^{22}$, —C(=O)N(R$^{22}$)$_2$, —CH$_2$OR$^{22}$, —OC(=O)R$^{22}$, —OC(=O)OR$^{22}$, —OR$^{22}$, —OC(=O)N(R$^{22}$)$_2$, —NR$^{22}$C(=O)R$^{22}$, —NR$^{22}$C(=O)OR$^{22}$, —N(R$^{22}$)$_2$, —N(R$^{22}$)$_3^+$, —NR$^{22}$C(=O)N(R$^{22}$)$_2$, —NR$^{22}$SO$_2$N(R$^{22}$)$_2$, —NR$^{22}$SO$_2$R$^{22}$, —SO$_3$H, —SO$_2$R$^{22}$, —SO$_2$N(R$^{22}$)$_2$, —PO$_3$H$_2$, —NHC(=NH)NHR$^{22}$, —C(=NH)NHR$^{22}$, NO$_2$, and —OCH$_2$CO$_2$H;

R$^{21}$ is independently selected at each occurrence from the group: =O, F, Cl, Br, I, —CF$_3$, —CN, —CO$_2$R$^{22}$, —C(=O)R$^{22}$, —C(=O)N(R$^{22}$)$_2$, —CH$_2$OR$^{22}$, —OC(=O)R$^{22}$, —OC(=O)OR$^{22}$, —OR$^{22}$, —OC(=O)N(R$^{22}$)$_2$, —NR$^{22}$C(=O)R$^{22}$, —NR$^{22}$C(=O)OR$^{22}$, —NR$^{22}$C(=O)N(R$^{22}$)$_2$, —NR$^{22}$SO$_2$N(R$^{22}$)$_2$, —NR$^{22}$SO$_2$R$^{22}$, —SO$_3$H, —SO$_2$R$^{22}$, —S(=O)R$^{22}$, —SO$_2$N(R$^{22}$)$_2$, —N(R$^{22}$)$_2$, —N(R$^{22}$)$_3^+$, —PO$_3$H$_2$, —NHC(=NH)NHR$^{22}$, —C(=NH)NHR$^{22}$, =NOR$^{22}$, NO$_2$, —C(=O)NHOR$^{22}$, —C(=O)NHN(R$^{22}$)$_2$, —OCH$_2$CO$_2$H;

R$^{22}$ is independently selected at each occurrence from the group: hydrogen and C$_1$–C$_6$ alkyl;

X$^1$ is independently selected at each occurrence from the group: CR$^{23}$ and N;

x$^2$ is independently selected at each occurrence from the group: CR$^{23}$, CR$^{23}$R$^{23}$, N, NR$^{23}$, O and S;

X$^3$ is independently selected at each occurrence from the group: C, CR$^{23}$, and N;

provided the total number of heteroatoms, X$^1$, X$^2$, and X$^3$ in each ring of the ligand, L$^3$, is 1, 2, 3, or 4;

Y is selected from the group: BR$^{23-}$, CR$^{23}$, (P=O), (P=S);

n is 0 or 1;

a, b, c, d, e and f indicate the positions of optional double bonds, provided that one of e and f is a double bond;

R$^{23}$ is independently selected at each occurrence from the group: H, C$_1$–C$_{10}$ alkyl substituted with 0–3 R$^{24}$, C$_2$–C$_{10}$ alkenyl substituted with 0–3 R$^{24}$, C$_2$–C$_{10}$ alkynyl substituted with 0–3 R$^{24}$, aryl substituted with 0–3 R$^{24}$, C$_1$–C$_{10}$ alkoxy substituted with 0–3 R$^{24}$, C$_{3-13}$ carbocycle substituted with 0–3 R$^{24}$, and R$^{24}$;

alternatively, two R$^{23}$ may be taken together with the atom or atoms to which they are attached to form a fused aromatic substituted with 0–3 R$^{24}$, C$_{5-7}$ carbocyclic ring substituted with 0–3 R$^{24}$ or 5–7 membered heterocyclic ring containing from 1–4 heteroatoms selected from N, O, and S and substituted with 0–3 R$^{24}$;

R$^{24}$ is independently selected at each occurrence from the group: =O, F, Cl, Br, I, —CF$_3$, —CN, —NO$_2$, —CO$_2$R$^{25}$, —C(=O)R$^{25}$, —C(=O)N(R$^{25}$)$_2$, —N(R$^{25}$)$_3^+$, —CH$_2$OR$^{25}$, —OC(=O)R$^{25}$, —OC(=O)OR$^{25}$, —OR$^{25}$, —OC(=O)N(R$^{25}$)$_2$, —NR$^{25}$C(=O)R$^{25}$, —NR$^{25}$C(=O)OR$^{25}$, —NR$^{25}$C(=O)N(R$^{25}$)$_2$, —NR$^{25}$SO$_2$N(R$^{25}$)$_2$, —NR$^{25}$SO$_2$R$^{25}$, —SO$_3$H, —SO$_2$R$^{25}$, —SO$_2$N(R$^{25}$)$_2$, —N(R$^{25}$)$_2$, —OCH$_2$CO$_2$H; and R$^{25}$ is independently selected at each occurrence from the group: hydrogen and C$_1$–C$_6$ alkyl;

R$^{26}$ and R$^{27}$ are independently selected from the group: H; C$_1$–C$_{10}$ alkyl; —CN; —CO$_2$R$^{31}$; —C(=O)R$^{31}$; —C(=O)N(R$^{31}$)$_2$; C$_2$–C$_{10}$ 1-alkene substituted with 0–3 R$^{30}$; C$_2$–C$_{10}$ 1-alkyne substituted with 0–3 R$^{30}$; aryl substituted with 0–3 R$^{30}$; unsaturated 5–10 membered heterocycle containing from 1–4 heteroatoms selected from N, O, and S and substituted with 0–3 R$^{30}$; and unsaturated C$_{3-13}$ carbocycle substituted with 0–3 R$^{30}$;

alternatively, R$^{26}$ and R$^{27}$, may be taken together with the divalent carbon radical to which they are attached to form:

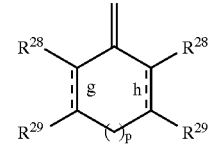

R$^{28}$ and R$^{29}$ are independently selected at each occurrence from the group: H; R$^{30}$; C$_1$–C$_{10}$ alkyl substituted with 0–3 R$^{30}$; C$_2$–C$_{10}$ alkenyl substituted with 0–3 R$^{30}$; C$_2$–C$_{10}$ alkynyl substituted with 0–3 R$^{30}$; aryl substituted with 0–3 R$^{30}$; 5–10 membered heterocycle containing from 1–4 heteroatoms selected from N, O, and S and substituted with 0–3 R$^{30}$; and C$_{3-13}$ carbocycle substituted with 0–3 R$^{30}$;

alternatively, R$^{28}$ and R$^{29}$ may be taken together to form a fused aromatic or 5–7 membered heterocyclic ring containing from 1–4 heteroatoms selected from N, O, and S;

g and h indicate the positions of optional double bonds and p is 0 or 1,

R$^{30}$ is independently selected at each occurrence from the group: =O, F, Cl, Br, I, —CF$_3$, —CN, —CO$_2$R$^{31}$, —C(=O)R$^{31}$, —C(=O)N(R$^{31}$)$_2$, —N(R$^{31}$)$_3^+$, —CH$_2$OR$^{31}$, —OC(=O)R$^{31}$, —OC(=O)OR$^{31}$, —OR$^{31}$, —OC(=O)N(R$^{31}$)$_2$, —NR$^{31}$C(=O)R$^{31}$, —NR$^{31}$C(=O)OR$^{31}$, —NR$^{31}$C(=O)N(R$^{31}$)$_2$, —NR$^{31}$SO$_2$N(R$^{31}$)$_2$, —NR$^{31}$SO$_2$R$^{31}$, —SO$_3$H, —SO$_2$R$^{31}$, —SR$^{31}$, —S(=O)R$^{31}$, —SO$_2$N(R$^{31}$)$_2$, —N(R$^{31}$)$_2$, —NHC (=NH)NHR$^{31}$, —C(=NH)NHR$^{31}$, =NOR$^{31}$, —C(=O)NHOR$^{31}$, —OCH$_2$CO$_2$H, 2-(1-morpholino)ethoxy; and R$^{31}$ is independently selected at each occurrence from the group: hydrogen, C$_1$–C$_6$ alkyl.

6. A kit according to claim 5, wherein:

the third ligand is selected from the group:

A$^1$, and 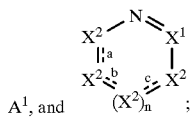;

R$^1$ is selected from the group: aryl substituted with 0–3 R$^3$, and 5–10 membered heterocycle containing from 1–4 heteroatoms selected from N, O, and S and substituted with 0–3 R$^3$;

R$^2$ is selected from the group: hydrogen, aryl substituted with 0–3 R$^3$, and 5–10 membered heterocycle containing from 1–4 heteroatoms selected from N, O, and S and substituted with 0–3 R$^3$;

R$^3$ is independently selected at each occurrence from the group: F, Cl, Br, I, —CO$_2$R$^4$, —C(=O)N(R$^4$)$_2$, —CH$_2$OR$^4$, —OC(=O)R$^4$, —OR$^4$, —NR$^4$C(=O) R$^4$, —NR$^4$SO$_2$R$^4$, —SO$_3$H, —SO$_2$N(R$^4$)$_2$, —N(R$^4$)$_2$, —N(R$^4$)$_3^+$, —NO$_2$, —OCH$_2$CO$_2$H, and C$_1$–C$_{10}$ alkyl substituted with 0–3 R$^5$;

R$^4$ is independently selected at each occurrence from the group: H, and C$_1$–C$_{10}$ alkyl substituted with 0–3 R$^5$;

R$^5$ is independently selected at each occurrence from the group: =O, F, Cl, Br, I, —CO$_2$R$^6$, —C(=O)N (R$^6$)$_2$, —CH$_2$OR$^6$, —OC(=O)R$^6$, —OR$^6$, —NR$^6$C (=O)R$^6$, —NR$^6$SO$_2$R$^6$, —SO$_3$H, —SO$_2$N(R$^6$)$_2$, —N(R$^6$)$_2$, —N(R$^6$)$_3^+$, —NO$_2$, —OCH$_2$CO$_2$H, and phenyl;

R$^7$ is selected from the group: hydrogen, and C$_1$–C$_{10}$ alkyl substituted with 0–3 R$^{15}$;

R$^8$ and R$^9$ are independently selected from the group: hydrogen, hydroxyl, and C$_1$–C$_{10}$ alkyl substituted with 0–3 R$^{15}$;

R$^{11}$ and R$^{12}$ are independently selected at each occurrence from the group: H, —OH, and C$_1$–C$_{10}$ alkyl substituted with 0–3 R$^{15}$;

m is 0–1;

R$^{14}$ is independently selected at each occurrence from the group: C$_1$–C$_5$ alkyl substituted with 0–3 R$^{15}$, F, Cl, Br, I, —CO$_2$R$^{16}$, —C(=O)N(R$^{16}$)$_2$, —CH$_2$OR$^{16}$, —OC(=O)R$^{16}$, —OR$^{16}$, —NR$^{16}$C (=O)R$^{16}$, —NR$^{16}$SO$_2$R$^{16}$, —SO$_3$H, —SO$_2$N(R$^{16}$)$_2$, —PO$_3$H$_2$, —NO$_2$, and —OCH$_2$CO$_2$H;

R$^{15}$ is independently selected at each occurrence from the group: =O, F, Cl, Br, I, —CO$_2$R$^{16}$, —C(=O) N(R$^{16}$)$_2$, —CH$_2$OR$^{16}$, —OC(=O)R$^{16}$, —OR$^{16}$, —NR$^{16}$C(=O)R$^{16}$, —NR$^{16}$SO$_2$R$^{16}$, —SO$_3$H, —SO$_2$N(R$^{16}$)$_2$, —PO$_3$H$_2$, and —OCH$_2$CO$_2$H;

A$^1$ is PR$^{17}$R$^{18}$R$^{19}$;

R$^{17}$, R$^{18}$, and R$^{19}$ are independently selected from the group: aryl substituted with 0–3 R$^{20}$, 5–10 membered heterocycle containing from 1–4 heteroatoms selected from N, O, and S and substituted with 0–3 R$^{20}$, and C$_1$–C$_{10}$ alkyl substituted with 0–3 R$^{21}$;

R$^{20}$ is independently selected at each occurrence from the group: C$_1$–C$_5$ alkyl substituted with 0–3 R$^{21}$, F, Cl, Br, I, —CO$_2$R$^{22}$, —C(=O)N(R$^{22}$)$_2$, —CH$_2$OR$^{22}$, —OC(=O)R$^{22}$, —OR$^{22}$, —NR$^{22}$C (=O)R$^{22}$, —NR$^{22}$SO$_2$R$^{22}$, —SO$_3$H, —SO$_2$N(R$^{22}$)$_2$, —N(R$^{22}$)$_2$, —N(R$^{22}$)$_3^+$, —PO$_3$H$_2$, and —OCH$_2$CO$_2$H;

R$^{21}$ is independently selected at each occurrence from the group: =O, F, Cl, Br, I, —CO$_2$R$^{22}$, —C(=O) N(R$^{22}$)$_2$, —CH$_2$OR$^{22}$, —OC(=O)R$^{22}$, —PO$_3$H$_2$, —OR$^{22}$, —NR$^{22}$C(=O)R$^{22}$, —NR$^{22}$SO$_2$R$^{22}$, —SO$_3$H, —SO$_2$N(R$^{22}$)$_2$, —N(R$^{22}$)$_2$, —N(R$^{22}$)$_3^+$, and —OCH$_2$CO$_2$H;

X$^2$ is independently selected at each occurrence from the group: CR$^{23}$, CR$^{23}$R$^{23}$, N, NR$^{23}$, and O;

provided the total number of heteroatoms, X$^1$, and X$^2$, is 1, 2, 3, or 4;

R$^{23}$ is independently selected at each occurrence from the group: H, C$_1$–C$_3$ alkyl substituted with 0–3 R$^{24}$, aryl substituted with 0–3 R$^{24}$, and R$^{24}$;

alternatively, two R$^{23}$ may be taken together with the atom or atoms to which they are attached to form a fused aromatic or a 5–7 membered heterocyclic ring containing from 1–4 heteroatoms selected from N, O, and S and substituted with 0–3 R$^{24}$; and R$^{24}$ is independently selected at each occurrence from the group: —NO$_2$, —CO$_2$R$^{25}$, —OR$^{25}$, —SO$_3$H, and —OCH$_2$CO$_2$H;

R$^{26}$ and R$^{27}$ are independently selected from the group: —CO$_2$R$^{31}$; C$_2$–C$_5$ 1-alkene substituted with 0–3 R$^{30}$; C$_2$–C$_5$, 1-alkyne substituted with 0–3 R$^{30}$; aryl substituted with 0–3 R$^{30}$; and unsaturated 5–10 membered heterocycle containing from 1–4 heteroatoms selected from N, O, and S and substituted with 0–3 R$^{30}$;

alternatively, R$^{26}$ and R$^{27}$, may be taken together with the divalent carbon radical to which they are attached to form:

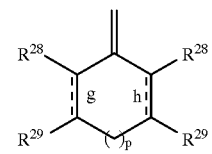

R$^{28}$ and R$^{29}$ may be independently selected from the group: H, and R$^{30}$;

alternatively, R$^{28}$, R$^{29}$ may be taken together to form a fused aromatic or a 5–7 membered heterocyclic ring containing from 1–4 heteroatoms selected from N, O, and S;

g and h indicate the positions of optional double bonds and p is 0 or 1,

R$^{30}$ is independently selected at each occurrence from the group: —CO$_2$R$^{31}$, —C(=O)N(R$^{31}$)$_2$, —CH$_2$OR$^{31}$, —OC(=O)R$^{31}$, —OR$^{34}$, —SO$_3$H, —N(R$^{34}$)$_2$, and —OCH$_2$CO$_2$H; and, R$^{31}$ is independently selected at each occurrence from the group: hydrogen, and C$_1$–C$_3$ alkyl.

7. A kit according to claim 6, wherein:

R$^1$ is selected from the group: aryl substituted with 0–1 R$^3$, and heterocycle substituted with 0–1 R$^3$, wherein said heterocycle is pyridine or phthalazine;

R$^2$ is selected from the group: hydrogen, and aryl substituted with 0–1 R$^3$;

R$^3$ is independently selected at each occurrence from the group: Cl, —CO$_2$R$^4$, —C(=O)N(R$^4$)$_2$, —OR$^4$, —SO$_3$H, and —NO$_2$;

R$^4$ is independently selected at each occurrence from the group: H, and C$_1$–C$_{10}$ alkyl substituted with 0–2 R$^5$;

$R^5$ is selected from the group: —$CO_2R^6$, —$OR^6$, and phenyl;

$R^6$ is independently selected from the group: H, and methyl;

$R^7$, $R^8$, and $R^9$ are hydrogen;

$R^{10}$ is selected from the group: —COOH, and 2-hydroxyphenyl;

m is 0–1, provided that when $R^{10}$ is —COOH, m is 1;

$R^{11}$, $R^{12}$, and $R^{13}$ are —$CH_2OH$;

$A^1$ is $PR^{17}R^{18}R^{19}$;

$R^{17}$, $R^{18}$, and $R^{19}$ are independently selected from the group: aryl substituted with 0–1 $R^{20}$, 5–10 membered heterocycle containing from 1–4 heteroatoms selected from N, O, and S and substituted with 0–1 $R^{20}$, and $C_1$–$C_3$ alkyl substituted with 0–1 $R^{21}$;

$R^{20}$ is independently selected at each occurrence from the group: —$CO_2R^{22}$, —$OR^{22}$, and —$SO_3H$;

$R^{21}$ is selected from the group: —$CO_2R^{22}$, and —$OR^{22}$;

$R^{22}$ is independently selected from the group: H, and methyl;

$X^1$ is CH;

$X^2$ is independently selected at each occurrence from the group: CH, and NH, provided only one $X^2$ is NH;

$R^{26}$ is selected from the group: —$CO_2R^{31}$; $C_2$–$C_3$ 1-alkene substituted with 0–1 $R^{30}$; aryl substituted with 0–1 $R^{30}$; unsaturated 5–10 membered heterocycle containing from 1–4 heteroatoms selected from N, O, and S and substituted with 0–1 $R^{30}$;

$R^{27}$ is H;

$R^{30}$ is independently selected at each occurrence from the group: —$CO_2R^{31}$, —$OR^{31}$, —$SO_3H$, and —$N(R^{31})_2$; and $R^{31}$ is independently selected at each occurrence from the group: hydrogen, and methyl.

8. A kit according to claim 7, wherein the kit, further comprises: a reducing agent.

9. A kit according to claim 8, wherein the reducing agent is Sn(II).

10. A kit according to claim 7, wherein the first ligand, the second ligand, and the third ligand are contained in one vial.

11. A method of imaging the heart in a mammal, comprising (i) administering an effective amount of a radiopharmaceutical of claim 1 and (ii) imaging said mammal using gamma scintigraphy.

12. A method of imaging the heart in a mammal, comprising (i) administering an effective amount of a radiopharmaceutical of claim 2 and (ii) imaging said mammal using gamma scintigraphy.

13. A method of imaging the heart in a mammal, comprising (i) administering an effective amount of a radiopharmaceutical of claim 3 and (ii) imaging said mammal using gamma scintigraphy.

14. A method of imaging the heart in a mammal, comprising (i) administering an effective amount of a radiopharmaceutical of claim 4 and (ii) imaging said mammal using gamma scintigraphy.

15. A method of imaging the brain in a mammal, comprising (i) administering an effective amount of a radiopharmaceutical of claim 1 and (ii) imaging said mammal using gamma scintigraphy.

16. A method of imaging the brain in a mammal, comprising (i) administering an effective amount of a radiopharmaceutical of claim 2 and (ii) imaging said mammal using gamma scintigraphy.

17. A method of imaging the brain in a mammal, comprising (i) administering an effective amount of a radiopharmaceutical of claim 3 and (ii) imaging said mammal using gamma scintigraphy.

18. A method of imaging the brain in a mammal, comprising (i) administering an effective amount of a radiopharmaceutical of claim 4 and (ii) imaging said mammal using gamma scintigraphy.

19. A method of imaging the lungs in a mammal, comprising (i) administering an effective amount of a radiopharmaceutical of claim 1 and (ii) imaging said mammal using gamma scintigraphy.

20. A method of imaging the lungs in a mammal, comprising (i) administering an effective amount of a radiopharmaceutical of claim 2 and (ii) imaging said mammal using gamma scintigraphy.

21. A method of imaging the lungs in a mammal, comprising (i) administering an effective amount of a radiopharmaceutical of claim 3 and (ii) imaging said mammal using gamma scintigraphy.

22. A method of imaging the lungs in a mammal, comprising (i) administering an effective amount of a radiopharmaceutical of claim 4 and (ii) imaging said mammal using gamma scintigraphy.

23. A method of imaging the hepatobiliary system in a mammal, comprising (i) administering an effective amount of a radiopharmaceutical of claim 1 and (ii) imaging said mammal using gamma scintigraphy.

24. A method of imaging the hepatobiliary system in a mammal, comprising (i) administering an effective amount of a radiopharmaceutical of claim 2 and (ii) imaging said mammal using gamma scintigraphy.

25. A method of imaging the hepatobiliary system in a mammal, comprising (i) administering an effective amount of a radiopharmaceutical of claim 3 and (ii) imaging said mammal using gamma scintigraphy.

26. A method of imaging the hepatobiliary system in a mammal, comprising (i) administering an effective amount of a radiopharmaceutical of claim 4 and (ii) imaging said mammal using gamma scintigraphy.

27. A method of imaging the kidneys in a mammal, comprising (i) administering an effective amount of a radiopharmaceutical of claim 1 and (ii) imaging said mammal using gamma scintigraphy.

28. A method of imaging the kidneys in a mammal, comprising (i) administering an effective amount of a radiopharmaceutical of claim 2 and (ii) imaging said mammal using gamma scintigraphy.

29. A method of imaging the kidneys in a mammal, comprising (i) administering an effective amount of a radiopharmaceutical of claim 3 and (ii) imaging said mammal using gamma scintigraphy.

30. A method of imaging the kidneys in a mammal, comprising (i) administering an effective amount of a radiopharmaceutical of claim 4 and (ii) imaging said mammal using gamma scintigraphy.

* * * * *